US007601820B2

(12) United States Patent
Wang et al.

(10) Patent No.: US 7,601,820 B2
(45) Date of Patent: *Oct. 13, 2009

(54) PREPARATION OF ALKYL-SUBSTITUTED 2-DEOXY-2-FLUORO-D-RIBOFURANOSYL PYRIMIDINES AND PURINES AND THEIR DERIVATIVES

(75) Inventors: Peiyuan Wang, Glen Rock, NJ (US); Wojciech Stec, Ksawerow (PL); Byoung-Kwon Chun, Robbinsville, NJ (US); Junxing Shi, Duluth, GA (US); Jinfa Du, New Hope, PA (US)

(73) Assignee: Pharmasset, Inc., Princeton, NJ (US)

( * ) Notice: Subject to any disclaimer, the term of this patent is extended or adjusted under 35 U.S.C. 154(b) by 115 days.

This patent is subject to a terminal disclaimer.

(21) Appl. No.: 11/353,597

(22) Filed: Feb. 13, 2006

(65) Prior Publication Data

US 2006/0199783 A1 Sep. 7, 2006

Related U.S. Application Data

(63) Continuation of application No. 11/185,988, filed on Jul. 21, 2005, now abandoned.

(51) Int. Cl.
*C07H 1/00* (2006.01)
*C07H 3/00* (2006.01)
*C07H 19/00* (2006.01)
*C07D 307/62* (2006.01)

(52) U.S. Cl. .................... 536/1.11; 536/22.1; 536/124; 549/314

(58) Field of Classification Search .................. None
See application file for complete search history.

(56) References Cited

U.S. PATENT DOCUMENTS

| | | |
|---|---|---|
| 3,798,209 A | 3/1974 | Witkowski et al. |
| RE29,835 E | 11/1978 | Witkowski |
| 4,957,924 A | 9/1990 | Beauchamp |
| 5,026,687 A | 6/1991 | Yarchoan et al. |
| 5,118,820 A | 6/1992 | Hertel .................... 549/313 |
| 5,149,794 A | 9/1992 | Yatvin et al. |
| 5,157,027 A | 10/1992 | Biller et al. |
| 5,194,654 A | 3/1993 | Hostetler et al. |
| 5,223,263 A | 6/1993 | Hostetler et al. |
| 5,256,641 A | 10/1993 | Yatvin et al. |
| 5,372,808 A | 12/1994 | Blatt et al. |
| 5,405,598 A | 4/1995 | Schinazi et al. |
| 5,411,947 A | 5/1995 | Hostetler et al. |
| 5,420,266 A | 5/1995 | Britton et al. |
| 5,462,724 A | 10/1995 | Schinazi et al. |
| 5,463,092 A | 10/1995 | Hostetler et al. |
| 5,496,546 A | 3/1996 | Wang et al. |
| 5,538,865 A | 7/1996 | Reyes et al. |
| 5,543,389 A | 8/1996 | Yatvin et al. |
| 5,543,390 A | 8/1996 | Yatvin et al. |
| 5,543,391 A | 8/1996 | Yatvin et al. |
| 5,554,728 A | 9/1996 | Basava et al. |
| 5,610,054 A | 3/1997 | Draper |
| 5,633,358 A | 5/1997 | Gruetzke et al. |
| 5,633,388 A | 5/1997 | Diana et al. |
| 5,676,942 A | 10/1997 | Testa et al. |
| 5,703,058 A | 12/1997 | Schinazi et al. |
| 5,711,944 A | 1/1998 | Gilbert et al. |
| 5,725,859 A | 3/1998 | Omer |
| 5,738,845 A | 4/1998 | Imakawa |
| 5,738,846 A | 4/1998 | Greenwald et al. |
| 5,747,646 A | 5/1998 | Hakimi et al. |
| 5,767,097 A | 6/1998 | Tam |
| 5,792,834 A | 8/1998 | Hakimi et al. |
| 5,830,455 A | 11/1998 | Valtuena et al. |
| 5,830,905 A | 11/1998 | Diana et al. |
| 5,834,594 A | 11/1998 | Hakimi et al. |
| 5,837,257 A | 11/1998 | Tsai et al. |
| 5,846,964 A | 12/1998 | Ozeki |
| 5,849,696 A | 12/1998 | Chretien et al. |
| 5,869,253 A | 2/1999 | Draper |
| 5,891,874 A | 4/1999 | Colacino et al. |
| 5,905,070 A | 5/1999 | Schinazi et al. |
| 5,908,621 A | 6/1999 | Glue et al. |
| 5,922,757 A | 7/1999 | Chojkier |
| 5,928,636 A | 7/1999 | Alber et al. |

(Continued)

FOREIGN PATENT DOCUMENTS

DE      19914474 A1      3/1998

(Continued)

OTHER PUBLICATIONS

Kotra, L.P. "Structure-Activity Relationships of 2'-Deoxy-2',2'-difluoro-L-crythro-pentofuranosyl Nucleosides," J. Med. Chem, 1997, vol. 40, pp. 3635-3644.
Hertel et al. "Synthesis of 2-Deoxy-2,2-difluoro-D-ribose and 2-Deoxy-2,2-difluoro-D-ribose and 2-Deoxy-2,2-difluoro-D-ribofuranosyl Nucleosides", 1988, vol. 53, pp. 2406-2409.
U.S. Appl. No. 60/392,350, filed May 21, 2001, Elek.
U.S. Appl. No. 60/392,351, filed Jun. 28, 2002, Storer.
Battaglia, A. et al., "Combination Therapy with Interferon and Ribavirin in the Treatment of Chronic Hepatitis C Infection," The Annals of Pharmacotherapy, vol. 34, No. 4, pp. 487-494 (Apr. 2000).
Berenguer, M. et al., "Hepatitis C virus in the transplant setting," Antiviral Therapy. Second International Conference on Therapies for Viral Hepatitis, vol. 3, Supplement 3, pp. 125-136 (1998).

(Continued)

*Primary Examiner*—Traviss C McIntosh, III
(74) *Attorney, Agent, or Firm*—Duane Morris LLP

(57) ABSTRACT

The present invention provides (i) a process for preparing a 2-deoxy-2-fluoro-2-methyl-D-ribonolactone derivative, (ii) conversion of the lactone to nucleosides with potent anti-HCV activity, and their analogues, and (iii) a method to prepare the anti-HCV nucleosides containing the 2-deoxy-2-fluoro-2-C-methyl-β-D-ribofuranosyl nucleosides from a preformed, preferably naturally-occurring, nucleoside.

18 Claims, No Drawings

U.S. PATENT DOCUMENTS

| | | | |
|---|---|---|---|
| 5,942,223 | A | 8/1999 | Bazer et al. |
| 5,980,884 | A | 11/1999 | Blatt et al. |
| 5,990,276 | A | 11/1999 | Zhang et al. |
| 6,004,933 | A | 12/1999 | Spruce et al. |
| 6,034,134 | A | 3/2000 | Gold et al. |
| 6,043,077 | A | 3/2000 | Barber et al. |
| 6,056,961 | A | 5/2000 | Lavie et al. |
| 6,090,932 | A | 7/2000 | McGee et al. |
| 6,130,326 | A | 10/2000 | Ramasamy et al. |
| 6,156,501 | A | 12/2000 | McGall et al. |
| 6,232,300 | B1 | 5/2001 | Schinazi et al. |
| 6,239,159 | B1 | 5/2001 | Brown et al. |
| 6,348,587 | B1 | 2/2002 | Schinazi et al. |
| 6,391,859 | B1 | 5/2002 | Schinazi et al. |
| 6,410,531 | B1 | 6/2002 | Llinas-Brunet et al. |
| 6,420,380 | B2 | 7/2002 | Llinas-Brunet et al. |
| 6,455,513 | B1 | 9/2002 | McGuigan et al. |
| 6,455,690 | B1 | 9/2002 | Tam et al. |
| 6,479,463 | B1 | 11/2002 | Wang et al. |
| 6,495,677 | B1 | 12/2002 | Ramasamy et al. |
| 6,509,320 | B1 | 1/2003 | Wang et al. |
| 6,534,523 | B1 | 3/2003 | Llinas-Brunet et al. |
| 6,552,183 | B1 | 4/2003 | Ramasamy et al. |
| 6,555,677 | B2 | 4/2003 | Petrillo et al. |
| 6,573,248 | B2 | 6/2003 | Ramasamy et al. |
| 6,642,206 | B2 | 11/2003 | Ramasamy et al. |
| 6,660,721 | B2 | 12/2003 | Devos et al. |
| 6,677,314 | B2 | 1/2004 | Klecker et al. |
| 6,677,315 | B2 | 1/2004 | Klecker et al. |
| 6,680,303 | B2 | 1/2004 | Schinazi et al. |
| 6,682,715 | B2 | 1/2004 | Klecker et al. |
| 6,683,045 | B2 | 1/2004 | Klecker et al. |
| 6,703,374 | B1 | 3/2004 | Klecker et al. |
| 6,753,309 | B2 | 6/2004 | Klecker et al. |
| 6,777,395 | B2 | 8/2004 | Bhat et al. |
| 6,787,305 | B1 | 9/2004 | Li et al. |
| 6,787,526 | B1 | 9/2004 | Bryant et al. |
| 6,815,542 | B2 | 11/2004 | Hong et al. |
| 6,897,201 | B2 | 5/2005 | Boyer et al. |
| 6,908,924 | B2 | 6/2005 | Watanabe et al. |
| 6,914,054 | B2 | 7/2005 | Sommadossi et al. |
| 6,962,991 | B2 | 11/2005 | Dempcy et al. |
| 7,018,985 | B1 | 3/2006 | Boyer et al. |
| 7,018,989 | B2 | 3/2006 | McGuigan et al. |
| 7,081,449 | B2 | 7/2006 | Pietrzkowski et al. |
| 2002/0058635 | A1 | 5/2002 | Averett |
| 2002/0198173 | A1 | 12/2002 | Schinazi et al. |
| 2003/0050229 | A1 | 3/2003 | Sommadossi et al. |
| 2003/0060400 | A1 | 3/2003 | LaColla et al. |
| 2003/0120071 | A1 | 6/2003 | McGuigan et al. |
| 2003/0144502 | A1 | 7/2003 | Pietrzkowski et al. |
| 2003/0153744 | A1 | 8/2003 | Mekouar et al. |
| 2004/0006007 | A1 | 1/2004 | Gosselin et al. |
| 2004/0014108 | A1 | 1/2004 | Elarup et al. |
| 2004/0023240 | A1 | 2/2004 | Marliere et al. |
| 2004/0023901 | A1 | 2/2004 | Cook et al. |
| 2004/0059104 | A1 | 3/2004 | Cook et al. |
| 2004/0063622 | A1 | 4/2004 | Sommadossi et al. |
| 2004/0067901 | A1 | 4/2004 | Bhat et al. |
| 2004/0072788 | A1 | 4/2004 | Bhat et al. |
| 2004/0097461 | A1 | 5/2004 | Sommadossi et al. |
| 2004/0097462 | A1 | 5/2004 | Sommadossi et al. |
| 2004/0101535 | A1 | 5/2004 | Sommadossi et al. |
| 2004/0102414 | A1 | 5/2004 | Sommadossi et al. |
| 2004/0110717 | A1 | 6/2004 | Carroll et al. |
| 2004/0167140 | A1 | 8/2004 | Schinazi et al. |
| 2004/0191824 | A1 | 9/2004 | Dempcy et al. |
| 2004/0214844 | A1 | 10/2004 | Otto et al. |
| 2004/0229839 | A1 | 11/2004 | Babu et al. |
| 2004/0248892 | A1 | 12/2004 | Wang |
| 2004/0254141 | A1 | 12/2004 | Schinazi et al. |
| 2004/0259934 | A1 | 12/2004 | Olsen et al. |
| 2004/0265969 | A1 | 12/2004 | Li et al. |
| 2004/0266996 | A1 | 12/2004 | Rabi |
| 2005/0009737 | A1 | 1/2005 | Clark |
| 2005/0020825 | A1* | 1/2005 | Storer et al. ............... 536/27.1 |
| 2005/0026853 | A1 | 2/2005 | Mekouar et al. |
| 2005/0031588 | A1 | 2/2005 | Sommadassi et al. |
| 2005/0075309 | A1 | 4/2005 | Storer et al. |
| 2005/0080034 | A1 | 4/2005 | Standring et al. |
| 2005/0090660 | A1 | 4/2005 | Watanabe et al. |
| 2005/0124532 | A1 | 6/2005 | Sommadossi et al. |
| 2005/0130931 | A1 | 6/2005 | Boyer et al. |
| 2005/0137161 | A1 | 6/2005 | Sommadossi et al. |
| 2005/0148534 | A1 | 7/2005 | Castellino et al. |
| 2005/0164960 | A1 | 7/2005 | Olsen et al. |
| 2005/0215513 | A1 | 9/2005 | Boojamra et al. |
| 2005/0227947 | A1 | 10/2005 | Chan et al. |
| 2005/0261237 | A1 | 11/2005 | Boojamra et al. |
| 2006/0003951 | A1 | 1/2006 | Mekouar et al. |
| 2006/0014943 | A1 | 1/2006 | Dempcy et al. |
| 2006/0035866 | A1 | 2/2006 | Cannizzaro et al. |
| 2006/0040944 | A1 | 2/2006 | Gosselin et al. |
| 2006/0079478 | A1 | 4/2006 | Boojamra et al. |
| 2006/0110727 | A9 | 5/2006 | McGall et al. |
| 2006/0122146 | A1 | 6/2006 | Chun et al. |
| 2006/0122154 | A1 | 6/2006 | Olsen et al. |
| 2006/0142238 | A1 | 6/2006 | McGuigan |
| 2006/0144502 | A1 | 7/2006 | Weder |
| 2007/0087960 | A1* | 4/2007 | Storer et al. .................... 514/8 |

FOREIGN PATENT DOCUMENTS

| | | |
|---|---|---|
| EP | 180276 A1 | 10/1984 |
| EP | 350287 B1 | 7/1989 |
| WO | WO8902733 A1 | 4/1989 |
| WO | WO9000555 A1 | 6/1989 |
| WO | WO9116920 A1 | 11/1991 |
| WO | WO9118914 A1 | 12/1991 |
| WO | WO9119721 A1 | 12/1991 |
| WO | WO9300910 A1 | 1/1993 |
| WO | WO9426273 A1 | 11/1994 |
| WO | WO9513090 A1 | 5/1995 |
| WO | WO 95/24185 | 9/1995 |
| WO | WO9615132 A1 | 5/1996 |
| WO | WO 96/32403 | 10/1996 |
| WO | WO9736554 A1 | 10/1997 |
| WO | WO 98/16184 | 4/1998 |
| WO | WO9817679 A1 | 4/1998 |
| WO | WO9822496 A2 | 5/1998 |
| WO | WO9822496 A3 | 5/1998 |
| WO | WO9907734 A2 | 2/1999 |
| WO | WO9907734 A3 | 2/1999 |
| WO | WO9915194 A1 | 4/1999 |
| WO | WO9932139 A1 | 7/1999 |
| WO | WO9932140 A1 | 7/1999 |
| WO | WO9943691 A1 | 9/1999 |
| WO | WO9959621 A1 | 11/1999 |
| WO | WO9964016 A1 | 12/1999 |
| WO | WO0009531 A2 | 2/2000 |
| WO | WO0024355 A1 | 5/2000 |
| WO | WO0037110 A2 | 6/2000 |
| WO | WO0037110 A3 | 6/2000 |
| WO | WO0132153 A2 | 5/2001 |
| WO | WO0160315 A3 | 8/2001 |
| WO | WO0160315 R4 | 8/2001 |
| WO | WO0179246 A2 | 10/2001 |
| WO | WO0179246 A3 | 10/2001 |
| WO | WO0179246 R4 | 10/2001 |
| WO | WO0181359 A1 | 11/2001 |
| WO | WO0190121 A3 | 11/2001 |
| WO | WO0190121 R4 | 11/2001 |
| WO | WO0191737 A2 | 12/2001 |
| WO | WO0192282 A3 | 12/2001 |

| | | |
|---|---|---|
| WO | WO0192282 R4 | 12/2001 |
| WO | WO0196353 A2 | 12/2001 |
| WO | WO0196353 A3 | 12/2001 |
| WO | WO0196353 R4 | 12/2001 |
| WO | WO0208187 A1 | 1/2002 |
| WO | WO0208187 R6 | 1/2002 |
| WO | WO0208198 A2 | 1/2002 |
| WO | WO0208198 A3 | 1/2002 |
| WO | WO0208198 R4 | 1/2002 |
| WO | WO0208251 A2 | 1/2002 |
| WO | WO0208251 A3 | 1/2002 |
| WO | WO0208251 R4 | 1/2002 |
| WO | WO0208256 A2 | 1/2002 |
| WO | WO0232414 A3 | 4/2002 |
| WO | WO0232414 R4 | 4/2002 |
| WO | WO0232920 A2 | 4/2002 |
| WO | WO0232920 A3 | 4/2002 |
| WO | WO0232920 R4 | 4/2002 |
| WO | WO 02/42172 | 6/2002 |
| WO | WO 02/49165 | 6/2002 |
| WO | WO0248116 A2 | 6/2002 |
| WO | WO0248157 A2 | 6/2002 |
| WO | WO0248157 A3 | 6/2002 |
| WO | WO0248157 R4 | 6/2002 |
| WO | WO0248165 A2 | 6/2002 |
| WO | WO0248165 A3 | 6/2002 |
| WO | WO0248165 R4 | 6/2002 |
| WO | WO0248172 A2 | 6/2002 |
| WO | WO0248172 A3 | 6/2002 |
| WO | WO0248172 R4 | 6/2002 |
| WO | WO02057425 A2 | 7/2002 |
| WO | WO02060926 A2 | 8/2002 |
| WO | WO02060926 A3 | 8/2002 |
| WO | WO02100415 A3 | 12/2002 |
| WO | WO02100415 R4 | 12/2002 |
| WO | WO02108415 A2 | 12/2002 |
| WO | WO03024461 A1 | 3/2003 |
| WO | WO 03/051899 | 6/2003 |
| WO | WO 03/053989 | 7/2003 |
| WO | WO 03/062256 | 7/2003 |
| WO | WO 03/068244 | 8/2003 |
| WO | WO 03/106477 | 12/2003 |
| WO | WO2004000858 A2 | 12/2003 |
| WO | WO2004000858 A3 | 12/2003 |
| WO | WO2004000858 R4 | 12/2003 |
| WO | WO 2004/009610 | 1/2004 |
| WO | WO2004002999 A2 | 1/2004 |
| WO | WO2004002999 A3 | 1/2004 |
| WO | WO2004002999 R4 | 1/2004 |
| WO | WO2004003000 A2 | 1/2004 |
| WO | WO2004003000 A3 | 1/2004 |
| WO | WO2004003000 R4 | 1/2004 |
| WO | WO2004003138 A2 | 1/2004 |
| WO | WO 2004/011478 | 2/2004 |
| WO | WO 2004/080466 | 9/2004 |
| WO | WO 2004/096234 | 11/2004 |
| WO | WO 2004/096235 | 11/2004 |
| WO | WO 2004/096286 | 11/2004 |
| WO | WO 2004/106356 | 12/2004 |
| WO | WO 2005/002626 | 1/2005 |
| WO | WO 2005/003147 | 1/2005 |
| WO | WO 2005/007810 | 1/2005 |
| WO | WO 2005008877 | 1/2005 |
| WO | WO 2005/009418 | 2/2005 |
| WO | WO 2005/012327 | 2/2005 |
| WO | WO 2005/020884 | 3/2005 |
| WO | WO 2005/021568 | 6/2005 |
| WO | WO 2005/072361 | 8/2005 |
| WO | WO 2006/000922 | 1/2006 |
| WO | WO 2006/029081 | 3/2006 |
| WO | WO 2006/031725 | 3/2006 |
| WO | WO 2006/037028 | 4/2006 |
| WO | WO 2006/061576 | 6/2006 |
| WO | WO 2006/065335 | 6/2006 |

OTHER PUBLICATIONS

Bhat, B. et al., "Synthesis and Pharmacokinetic Properties of Nucleoside Analogues as Possible Inhibitors of HCV RNA Replication," (Oral Session V: Hepatitis C Virus, Flaviviruses), 16th International Conference on Antiviral Research, Abstract No. 120, p. A75 (Apr. 27-May 1, 2003, Savannah, GA).

Chu, M. et al., "Isolation and structure of Sch 351633: A novel hepatitis C virus (HCV) NS3 protease inhibitor from the fungus Penicillium griseofulvum," Bioorganic & Medicinal Chemistry Letters, vol. 9, pp. 1949-1952 (1999).

Chu, M. et al., "Structure of Sch 68631: A New Hepatitis C Virus Proteinase Inhibitor from Streptomyces sp.," Tetrahedron Letters, vol. 37, No. 40, pp. 7229-7232 (Sep. 30, 1996).

Clark, J. et al., "Design, Synthesis, and Antiviral Activity of 2'-Deoxy-2'-fluoro-2'-C-methylcytidine, a Potent Inhibitor of Hepatitis C Virus Replication," Journal of Medicinal Chemistry, vol. 48, No. 17, pp. 5504-5508 (2005).

Davis, G. L., "Current Therapy for Chronic Hepatitis C," Gastroenterology 118: S104-S114, 2000.

De Lombaert, S. et al., "N-Phosphonomethyl Dipeptides and their Phosphonate Prodrugs, a New Generation of Neutral Endopeptidase (NEP, EC 3.4.24.11) Inhibitors," J. Med. Chem., vol. 37, No. 4, pp. 498-511(1994).

Edmundson et al., "Cyclic Organophophorus Compounds Part 23. Configurational Assignments in the 4-Phenyl-1,3,2$\lambda^5$-dioxaphosphorinane Series. X-Ray Molecular Structure of cis-2-Benzylamino-4-phenyl-1,3,2-dioxaphosphorinane 2-Oxide," J. Chem. Res. Synop., 1989, 5:122.

Eldrup, A. et al., "Structure Activity Relationship of 2' Modified Nucleosides for Inhibition of Hepatitis C Virus," (Oral Session V: Hepatitis C Virus, Flaviviruses), 16th International Conference on Antiviral Research, Abstract No. 119, p. A75 (Apr. 27-May 1, 2003, Savannah, Ga).

Eldrup, A. et al., "Structure-Activity Relationship of Purine Ribonucleosides for Inhibition of Hepatitis C Virus RNA-Dependent RNA Polymerase," J. Med. Chem., vol. 47, No. 9, pp. 2283-2295 (2004).

Farquhar, D. et al., "Synthesis and Biological Evaluation of Neutral Derivatives of 5-Fluoro-2'-deoxyuridine 5'-Phosphate," J. Med. Chem., vol. 26, No. 8, pp. 1153-1158 (Aug. 1983).

Freed, J. et al., "Evidence for acyloxymethyl esters of pyrimidine 5'-deoxyribonucleotides as extracellular sources of active 5'-deoxyribonucleotides in cultured cells," Biochemical Pharmacology, vol. 38, No. 19, pp. 3193-3198 (Oct. 1, 1989).

Farquhar, D. et al., "Synthesis of Biological Evaluation of 9-[5'-(2-Oxo-1,3,2-oxazaphosphorinan-2-yl)-β-D-arabinosyl]adenine and 9-[5'-(2-Oxo-1,3,2-dioxaphosphorinan-2-yl)- β-D-arabinosyl]adenine: Potential Nuetral Precursors of 9-[β-D-Arabinofuranosyl]adenine 5'-Monophosphate," J. Med. Chem., vol. 28, No. 9, pp. 1358-1361 (Sep. 1985).

Hertel, et al. "Synthesis of 2-Deoxy-2,2-difluoro-D-ribose and 2-Deoxy-2,2-difluoro-D-ribofuranosyl Necleosides," J. Org. Chem. vol. 53, pp. 2406-2409, (1988).

Hostetler, K. et al., "Greatly Enhanced Inhibition of Human Immunodeficiency Virus Type I Replication in CEM and HT4-6C Cells by 3'-Deoxythymidine Diphosphate Dimyristoylglycerol, a Lipid Prodrug of 3'-Deoxythymidine," Antimicrob. Agents Chemother., vol. 36, No. 9, pp. 2025-2029 (Sep. 1992).

Hostetler, K. et al., "Synthesis and Antiretroviral Activity of Phospholipid Analogs of Azidothymidine and Other Antiviral Nucleosides," J. Biol. Chem., vol. 265, No. 11, pp. 6112-6117 (Apr. 15, 1990).

Hunston, R. et al., "Synthesis and Biological Properties of Some Cyclic Phosphotriesters Derived from 2'-Deoxy-5-fluorouridine," J. Med. Chem., vol. 27, No. 4, pp. 440-444 (Apr. 1984).

Jones, R. et al., "Minireview: Nucleotide prodrugs," Antiviral Research, vol. 27, pp. 1-17 (1995).

Khamnei, S. et al., "Neighboring Group Catalysis in the Design of Nucleotide Prodrugs," J. Med. Chem., vol. 39, No. 20, pp. 4109-4115 (1996).

Kotra, L.P., "Structure-Activity Relationships of 2'-Deoxy-2',2'-difluoro-L-erythro-pentofuranosyl Nucleosides," J. Med. Chem., vol. 40, pp. 3635-3644, (1997).

Kryuchkov, A. A., et al, "Academy of Sciences of the USSR, Division of Chemical Science," 1987 Plenum Publishing Corporation, vol. 36, No. 6, Part 1, Jun. 1987, pp. 1145-1148.

Kryuchkov, A. et al., "Influence of Solvent on the Strength of Cyclic Oxygen-Containing Phosphorus Acids," Bulletin of the Academy of Sciences of the USSR. Division of Chemical Science, vol. 36, No. 6, Part 1, pp. 1145-1148(1987).

Kucera, L. et al., "Novel Membrane-Interactive Ether Lipid Analogs that Inhibit Infectious HIV-1 Production and Induce Defective Virus Formation," AIDS Research and Human Retroviruses, vol. 6, No. 4, pp. 491-501 (Apr. 1990).

Meier, C. et al., "Cyclic Saligenyl Phosphotriesters of 2',3'-Dideoxy-2',3'-didehydrothymidine (d4T)—A New Pro-Nucleotide Approach," Bioorganic & Medicinal Chemistry Letters, vol. 7, No. 2, pp. 99-104 (1997).

Mitchell, A. et al., "Bioreversible Protection for the Phospho Group: Bioactivation of the Di(4-acyloxybenzyl) and Mono(4-acyloxybenzyl) Phosphoesters of Methylphosphonate and Phosphonoacetate," Journal of the Chemical Society, Perkin Transactions 1, No. 18, pp. 2345-2353 (Sep. 21, 1992).

Neidlein, R. et al., "Mild preparation of I-benzyloxyminoalkylphosphonic dichlorides: Application to the synthesis of cyclic phosphonic diesters and cyclic monoester amides," Heterocycles, vol. 35, No. 2, pp. 1185-1203 (1993).

Nifantyev, E. et al., "Synthesis and structure of some stable phospholane-phospholanes," Phosphorus, Sulfur, and Silicon and the Related Elements, vol. 113, pp. 1-13 (1996).

Olsen, D. et al., "2'-Modified Nucleoside Analogs as Inhibitors of Hepatitis C RNA Replication," (Oral Session V: Hepatitis C Virus, Flaviviruses), 16th International Conference on Antiviral Research, Abstract No. 121, p. A76 (Apr. 27-May 1, 2003, Savannah, Ga)).

Piantadosi, C. et al., "Synthesis and Evaluation of Novel Ether Lipid Nucleoside Conjugates for Anti-HIV-1 Activity,", J. Med. Chem., vol. 34, No. 4, pp. 1408-1414 (1991).

Shih, Y. et al., "Preparation and Structures of 2-Dimethylamino-4-phenyl-1,3,2-dioxaphosphorinane-2-oxides," Bull. Inst. Chem. Academia Sinica, No. 41, pp. 9-16 (Mar. 1994).

Starrett, Jr., J. et al., "Synthesis, Oral Bioavailability Determination, and in Vitro Evaluation of Prodrugs of the Antiviral Agent 9-[2-(Phosphonomethoxy)ethyl]adenine (PMEA)," J. Med. Chem., vol. 37, No. 12, pp. 1857-1864 (1994).

Stuyver, L. et al., "Dynamics of Subgenomic Hepatitis C Virus Replicon RNA Levels in Huh-7 Cells after Exposure to Nucleoside Antimetabolites," Journal of Virology, vol. 77, No. 19, pp. 10689-10694 (Oct. 2003).

Stuyver, L. et al., "Inhibition of the Subgenomic Hepatitis C Virus Replicon in Huh-7 Cells by 2'-Deoxy-2'-fluorocytidine," Antimicrob. Agents Chemother., vol. 48, No. 2, pp. 651-654 (Feb. 2004).

Stuyver, L. et al., "Ribonucleoside Analogue that Blocks Replication of Bovine Viral Diarrhea and Hepatitis C in Viruses in Culture," Antimicrob. Agents Chemother., vol. 47, No. 1, pp. 244-254 (Jan. 2003).

Zon, G., "4 Cyclophosphamide Analogues," Progress in Medicinal Chemistry, vol. 19, pp. 205-246 (1982).

Novak, J.J.K. et al., "Nucleic Acid Components and Their Analogs. CXLIII. Nucleosides Derived from 2-Deoxy-2(R)-C-Methyl-Erythro-D-Pentose," Collection of Czechoslovak Chemical Communications, vol. 36, pp. 3670-3677 (1971).

Novak, J.J.K. et al., "Chiroptical Properties of 2-Methyl-1,4-Lactones; Revised Absolute Configuration of 2-Deoxy-2-C-Methyl-Erythro- D-Pentono-1,4-Lactones," Collection of Czechoslovak Chemical Communications, vol. 39, pp. 869-882 (1974).

* cited by examiner

PREPARATION OF ALKYL-SUBSTITUTED 2-DEOXY-2-FLUORO-D-RIBOFURANOSYL PYRIMIDINES AND PURINES AND THEIR DERIVATIVES

CROSS-REFERENCE TO RELATED APPLICATIONS

This patent application is a continuation of U.S. patent application Ser. No. 11/185,988, entitled "PREPARATION OF ALKYL-SUBSTITUTED 2-DEOXY-2-FLUORO-D-RIBOFURANOSYL PYRIMIDINES AND PURINES AND THEIR DERIVATIVES," filed on Jul. 21, 2005 now abandoned and assigned to the same assignee as this application. The aforementioned patent application is expressly incorporated herein by reference.

FIELD OF THE INVENTION

The present invention provides (i) a process for preparing a 2-deoxy-2-fluoro-2-methyl-D-ribonolactone derivative, (ii) conversion of the lactone to nucleosides with potent anti-HCV activity, and their analogues, and (iii) a method to prepare the anti-HCV nucleosides containing the 2'-deoxy-2'-fluoro-2'-C-methyl-β-D-ribofuranosyl nucleosides from a preformed, preferably naturally-occurring, nucleoside.

BACKGROUND OF THE INVENTION

In light of the fact that HCV infection has reached epidemic levels worldwide, and has tragic effects on the infected patients. Presently there is no universally effective treatment for this infection and the only drugs available for treatment of chronic hepatitis C are various forms of alpha interferon (IFN-α), either alone or in combination with ribavirin. However, the therapeutic value of these treatments has been compromised largely due to adverse effects, which highlights the need for development of additional options for treatment.

HCV is a small, enveloped virus in the Flaviviridae family, with a positive single-stranded RNA genome of ~9.6 kb within the nucleocapsid. The genome contains a single open reading frame (ORF) encoding a polyprotein of just over 3,000 amino acids, which is cleaved to generate the mature structural and nonstructural viral proteins. ORF is flanked by 5' and 3' non-translated regions (NTRs) of a few hundred nucleotides in length, which are important for RNA translation and replication. The translated polyprotein contains the structural core (C) and envelope proteins (E1, E2, p7) at the N-terminus, followed by the nonstructural proteins (NS2, NS3, NS4A, NS4B, NS5A, NS5B). The mature structural proteins are generated via cleavage by the host signal peptidase. The junction between NS2 and NS3 is autocatalytically cleaved by the NS2/NS3 protease, while the remaining four junctions are cleaved by the N-terminal serine protease domain of NS3 complexed with NS4A. The NS3 protein also contains the NTP-dependent helicase activity which unwinds duplex RNA during replication. The NS5B protein possesses RNA-dependent RNA polymerase (RDRP) activity, which is essential for viral replication. It is emphasized here that, unlike HBV or HIV, no DNA is involved in the replication of HCV.

U.S. patent application (Ser. No. 10/828,753) discloses that 1-(2-deoxy-2-fluoro-2-C-methyl-β-D-ribofuranosyl)cytosine (14) is a potent and selective anti-HCV agent. The original synthetic procedures (Schemes 1-3) are quite inefficient, with overall yields at or below 4% and are not amenable to large-scale.

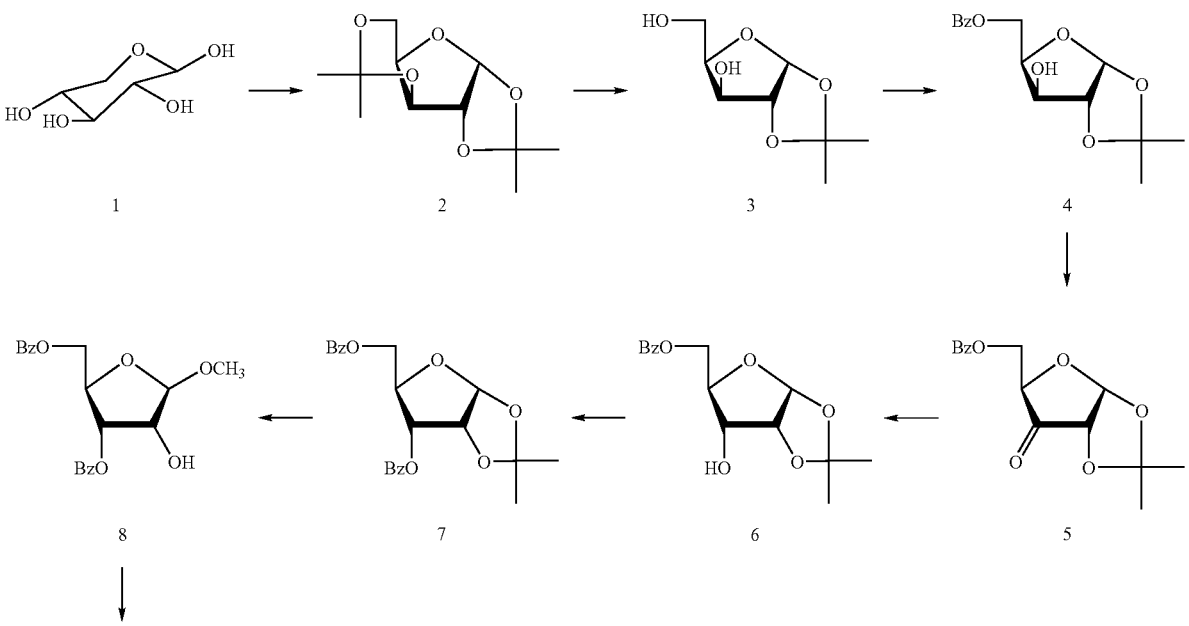

Scheme 1

-continued
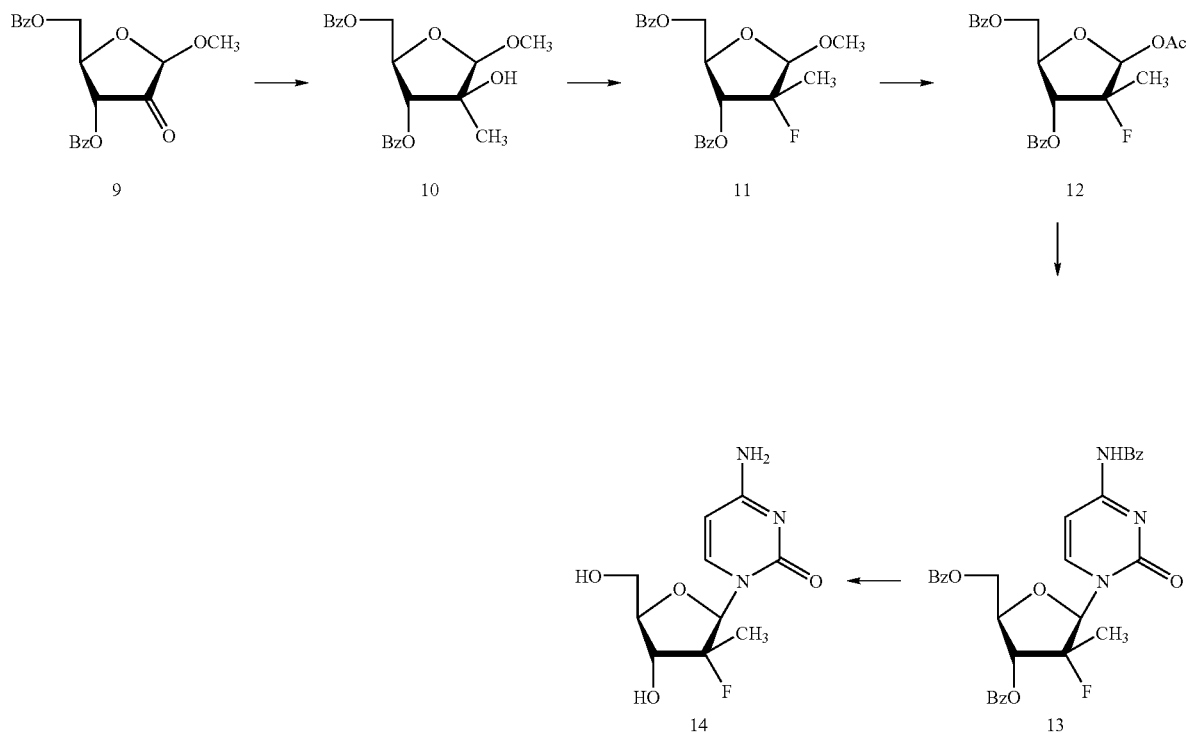
Scheme 2
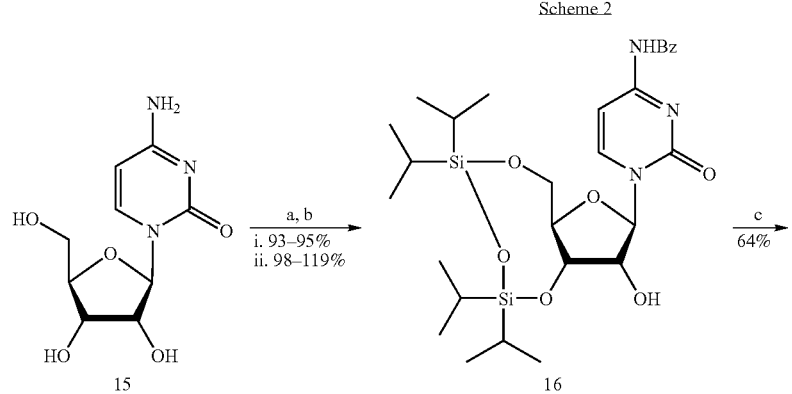

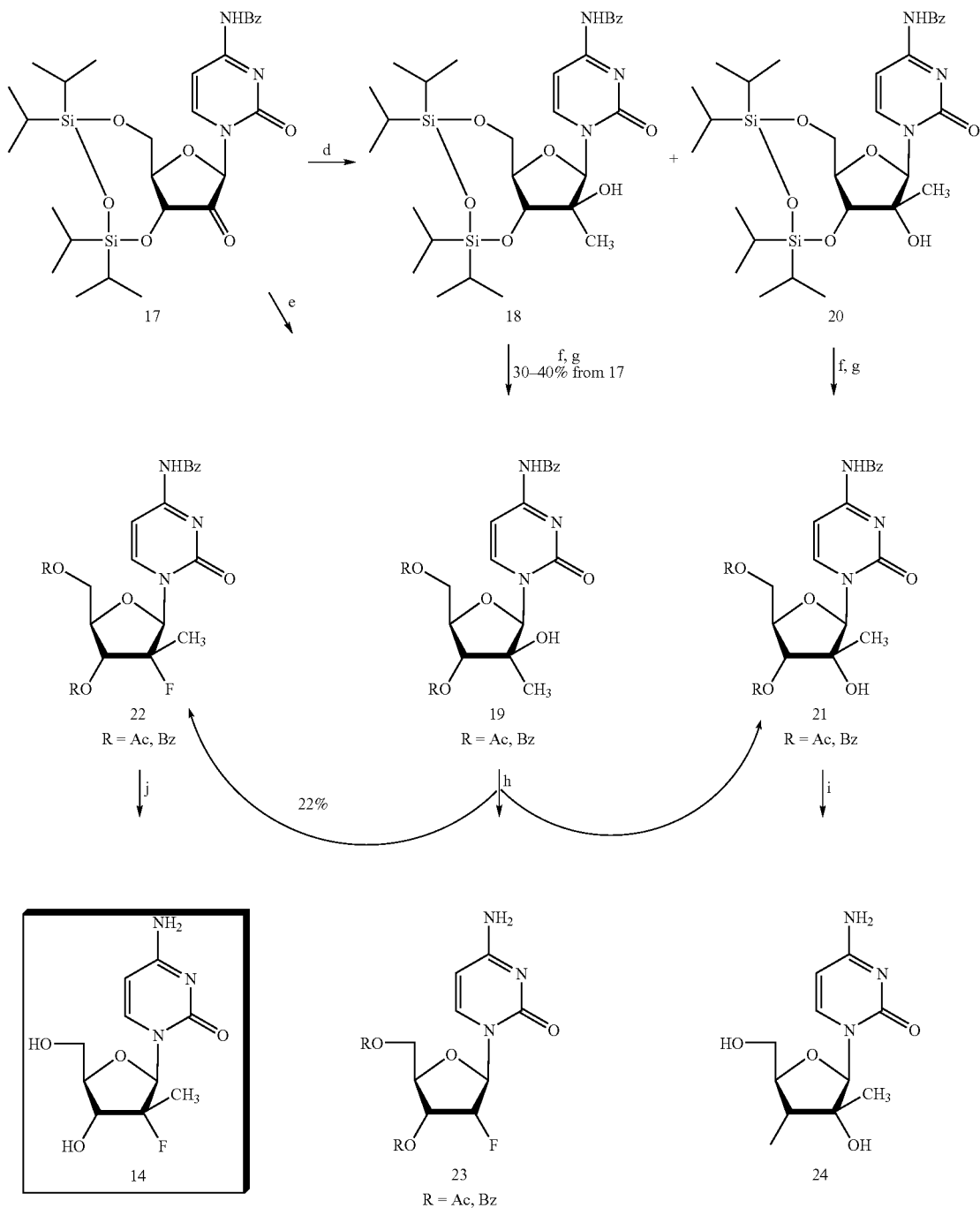
-continued
Reagents: a) Bz₂O/DMF; b) TIPDSCl₂/pyridine; c) COCl₂/DMSO/-78° C.; d) MeLi/Et₂O, -78° C.; e) MeMgBr/Et₂O; f) TBAF/THF; g) BzCl/py; or Ac₂O/py; h) DAST/Toluene; i) NH₃/MeOH

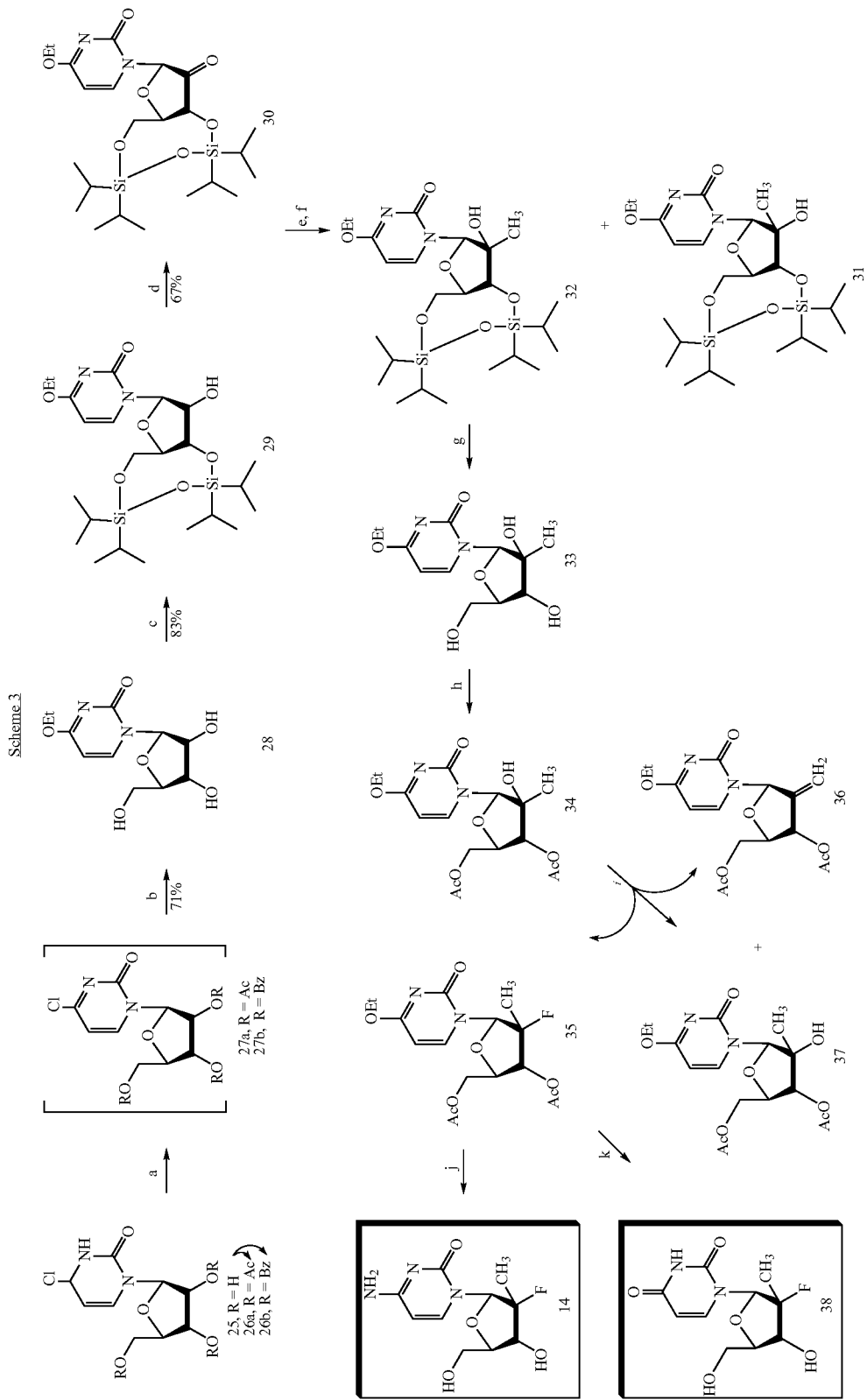

What is needed is a novel and cost effective process for the synthesis of 2-C-alkyl-2-deoxy-2-substituted-D-ribopyranosyl nucleosides that have activity against HCV.

SUMMARY OF INVENTION

The present invention as disclosed herein relates to the composition and synthetic methods of compounds of general formulas [I] and [II],

I

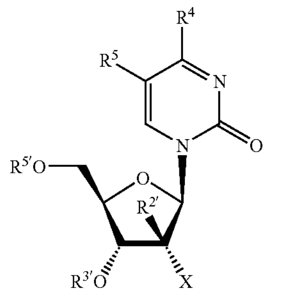

II 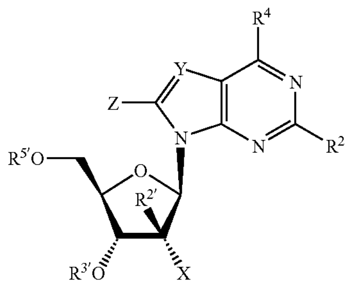 wherein

X is halogen (F, Cl, Br),

Y is N or CH,

Z is, halogen, OH, OR', SH, SR', $NH_2$, NHR', or R'

$R^{2'}$ is alkyl of $C_1$-$C_3$, vinyl, or ethynyl;

$R^{3'}$ and $R^{5'}$ can be same or different H, alkyl, aralkyl, acyl, cyclic acetal such as 2',3'-O-isopropylidene or 2',3-O-benzylidene, or 2',3'-cyclic carbonate;

$R^2$, $R^4$, and $R^5$ are independently H, halogen including F, Cl, Br, I, OH, OR', SH, SR', $N_3$, $NH_2$, NHR', $NR'_2$, NHC(O)OR', lower alkyl of $C_1$-$C_6$, halogenated (F, Cl, Br, I) lower alkyl of $C_1$-$C_6$ such as $CF_3$ and $CH_2CH_2F$, lower alkenyl of $C_2$-$C_6$ such as $CH{=}CH_2$, halogenated (F, Cl, Br, I) lower alkenyl of $C_2$-$C_6$ such as CH═CHCl, CH═CHBr and CH═CHI, lower alkynyl of $C_2$-$C_6$ such as C≡CH, halogenated (F, Cl, Br, I) lower alkynyl of $C_2$-$C_6$, hydroxy lower alkyl of $C_1$-$C_6$ such as $CH_2OH$ and $CH_2CH_2OH$, halogenated (F, Cl, Br, I) lower alkyl of $C_1$-$C_6$, lower alkoxy of $C_1$-$C_6$ such as methoxy and ethoxy, $CO_2H$, $CO_2R'$. $CONH_2$, CONHR', $CONR'_2$, $CH{=}CHCO_2H$, $CH{=}CHCO_2R'$; and, R' is an optionally substituted alkyl of $C_1$-$C_{12}$ (particularly when the alkyl is an amino acid residue), cycloalkyl, optionally substituted alkynyl of $C_2$-$C_6$, optionally substituted lower alkenyl of $C_2$-$C_6$, or optionally substituted acyl.

In other aspects, the present invention provides methods to prepare nucleosides containing the 2-deoxy-2-fluoro-2-C-methyl-D-ribofuranosyl moiety of general structures of III and IV,

III

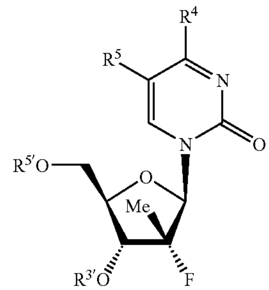

IV 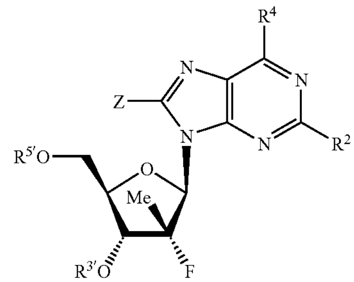 through (i) synthesis of the 3,5-protected 2-deoxy-2-fluoro-2-C-methyl-D-ribono-γ-lactone intermediate of general structure V, (ii) conversion of V into purine and pyrimidine nucleosides of general structures of III and IV, and (iii) preparation of nucleosides of general structures of III and IV from preformed, preferably natural, nucleosides.

V

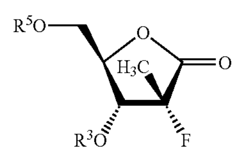

Regarding III, IV and V above, $R^4$ and $R^5$ are as defined above and $R^3$ and $R^5$ can be independently H, Me, Acyl (such as Ac, Bz, substituted Bz), benzyl, substituted benzyl, Trityl, Trialkylsilyl, t-Butyldialkylsilyl, t-Butyldiphenylsilyl, TIPDS, THP, MOM, MEM, or $R^3$ and $R^5$ are linked through —$SiR_2$—O—$SiR_2$— or —$SiR_2$—, wherein R is a lower alkyl group such as Me, Et, n-Pr or i-Pr.

Still another aspect of the present invention are the novel lactone intermediates of formula V and processes for the preparation of the lactone intermediates as detailed below, including precursor ester intermediates as also detailed below.

DETAILED DESCRIPTION

Presently no preventive means against Flaviviridae, including hepatitis C virus (HCV), Dengue virus (DENV), West Nile virus (WNV) or Yellow Fever virus (YFV), infection is available. The only approved therapies are for treatment of HCV infection with alpha interferon alone or in combination with the nucleoside ribavirin, but the therapeutic value of these treatments has been compromised largely due to adverse effects. It was recently discovered that a group of nucleosides, including 2'-deoxy-2'-fluoro-2'-C-methylcytidine (14), exhibit potent and selective activity against replication of HCV in a replicon system. However, the difficulty of chemical synthesis of this and analogous nucleosides impedes further biophysical, biochemical, pharmacological evaluations mandatory for development of clinical drugs for treatment of Flaviviridae infection.

The present invention provides an efficient preparation of nucleosides containing the 2-deoxy-2-fluoro-2-C-methyl-D-ribofuranosyl moiety III and IV, through (i) synthesis of intermediate the 3,5-protected 2-deoxy-2-fluoro-2-C-methyl-D-ribono-γ-lactone of general structure V, (ii) conversion of V into purine and pyrimidine nucleosides of general structures of III and IV, and (iii) preparation of nucleosides of general structures of III and IV from preformed, preferably natural, nucleosides.

DEFINITIONS

The term "independently" is used herein to indicate that the variable, which is independently applied, varies independently from application to application. Thus, in a compound such as $R^aXYR^a$, wherein $R^a$ is "independently carbon or nitrogen", both $R^a$ can be carbon, both $R^a$ can be nitrogen, or one $R^a$ can be carbon and the other $R^a$ nitrogen.

As used herein, the terms "enantiomerically pure" or "enantiomerically enriched" refers to a nucleoside composition that comprises at least approximately 95%, and preferably approximately 97%, 98%, 99% or 100% of a single enantiomer of that nucleoside.

As used herein, the term "substantially free of" or "substantially in the absence of" refers to a nucleoside composition that includes at least 85 or 90% by weight, preferably 95% to 98% by weight, and even more preferably 99% to 100% by weight, of the designated enantiomer of that nucleoside. In a preferred embodiment, in the methods and compounds of this invention, the compounds are substantially free of enantiomers.

The term "alkyl," as used herein, unless otherwise specified, refers to a saturated straight or branched hydrocarbon chain of typically $C_1$ to $C_{10}$, and specifically includes methyl, ethyl, propyl, isopropyl, butyl, isobutyl, t-butyl, pentyl, isopentyl, neopentyl, hexyl, isohexyl, cyclohexyl, cyclohexylmethyl, 3-methylpentyl, 2,2-dimethylbutyl, and 2,3-dimethylbutyl, and the like. The term includes both substituted and unsubstituted alkyl groups. Alkyl groups can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate. One or more of the hydrogen atoms attached to carbon atom on alkyl may be replaces by one or more halogen atoms, e.g. fluorine or chlorine or both, such as trifluoromethyl, difluoromethyl, fluorochloromethyl, and the like. The hydrocarbon chain may also be interrupted by a heteroatom, such as N, O or S.

The term "lower alkyl," as used herein, and unless otherwise specified, refers to a $C_1$ to $C_4$ saturated straight or branched alkyl group, including both substituted and unsubstituted forms as defined above. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term "cycloalkyl", as used herein, unless otherwise specified, refers to a saturated hydrocarbon ring having 3-8 carbon atoms, preferably, 3-6 carbon atoms, such as cyclopropyl, cyclobutyl, cyclopentyl and cyclohexyl. The cycloalkyl group may also be substituted on the ring by and alkyl group, such as cyclopropylmethyl and the like.

The terms "alkylamino" or "arylamino" refer to an amino group that has one or two alkyl or aryl substituents, respectively.

The term "protected," as used herein and unless otherwise defined, refers to a group that is added to an oxygen, nitrogen, or phosphorus atom to prevent its further reaction or for other purposes. A wide variety of oxygen and nitrogen protecting groups are known to those skilled in the art of organic synthesis. Non-limiting examples include: C(O)-alkyl, C(O)Ph, C(O)aryl, $CH_3$, $CH_2$-alkyl, $CH_2$-alkenyl, $CH_2Ph$, $CH_2$-aryl, $CH_2O$-alkyl, $CH_2O$-aryl, $SO_2$-alkyl, $SO_2$-aryl, tert-butyldimethylsilyl, tert-butyldiphenylsilyl, and 1,3-(1,1,3,3-tetraisopropyldisiloxanylidene).

The term "aryl," as used herein, and unless otherwise specified, refers to phenyl, biphenyl, or naphthyl, and preferably phenyl. The term includes both substituted and unsubstituted moieties. The aryl group can be substituted with one or more substituents, including, but not limited to hydroxyl, halo, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in T. W. Greene and P. G. M. Wuts, "Protective Groups in Organic Synthesis," 3rd ed., John Wiley & Sons, 1999.

The terms "alkaryl" or "alkylaryl" refer to an alkyl group with an aryl substituent. The terms "aralkyl" or "arylalkyl" refer to an aryl group with an alkyl substituent, as for example, benzyl.

The term "halo," as used herein, includes chloro, bromo, iodo and fluoro.

The term "acyl ester" or "O-linked ester" refers to a carboxylic acid ester of the formula C(O)R' in which the non-carbonyl moiety of the ester group, R', is a straight or branched alkyl, or cycloalkyl or lower alkyl, alkoxyalkyl including methoxymethyl, aralkyl including benzyl, aryloxyalkyl such as phenoxymethyl, aryl including phenyl optionally substituted with halogen (F, Cl, Br, I), $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally include a phenyl group.

The term "acyl" refers to a group of the formula R"C(O)—, wherein R" is a straight or branched alkyl, or cycloalkyl, amino acid, aryl including phenyl, alkylaryl, aralkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxy-trityl, substituted benzyl, alkaryl, aralkyl including benzyl, alkoxyalkyl including methoxymethyl, aryloxyalkyl such as phenoxymethyl. Aryl groups in the esters optimally comprise a phenyl group. In particular, acyl groups include acetyl, trifluoroacetyl, methylacetyl, cyclopropylacetyl, cyclopropyl carboxy, propionyl, butyryl, hexanoyl, heptanoyl, octanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoro-heptanoyl, 7H-dodeca-fluoroheptanoyl, 7-chlorododecafluoro-heptanoyl, 7-chloro-dodecafluoro-heptanoyl, 7H-dodecafluoro-heptanoyl, 7H-dodeca-fluoroheptanoyl, nona-fluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxy-benzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl. When the term acyl is used, it is meant to be a specific and independent disclosure of acetyl, trifluoroacetyl, methylacetyl, cyclopropylacetyl, propionyl, butyryl, hexanoyl, heptanoyl, octanoyl, neo-heptanoyl, phenylacetyl, diphenylacetyl, ct-trifluoromethyl-phenylacetyl, bromoacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, 2-thiopheneacetyl, tert-butylacetyl, trichloroacetyl, monochloro-acetyl, dichloroacetyl, methoxybenzoyl, 2-bromo-propionyl, decanoyl, n-pentadecanoyl, stearyl, 3-cyclopentyl-propionyl, 1-benzene-carboxyl, pivaloyl acetyl, 1-adamantane-carboxyl, cyclohexane-carboxyl, 2,6-pyridinedicarboxyl, cyclopropane-carboxyl, cyclobutane-carboxyl, 4-methylbenzoyl, crotonyl, 1-methyl-1H-indazole-3-carbonyl, 2-propenyl, isovaleryl, 4-phenylbenzoyl.

The term "lower acyl" refers to an acyl group in which R", above defined, is lower alkyl.

The term "purine" or "pyrimidine" base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-alcylaminopurine, $N^6$-thioallcyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-iodopyrimidine, $C^6$-Iodo-pyrimidine, $C^5$—Br-vinyl pyrimidine, $C^6$—Br-vinyl pyriniidine, $C^5$-nitropyrimidine, $C^5$-amino-pyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term "amino acid" includes naturally occurring and synthetic α, β, γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleucinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. When the term amino acid is used, it is considered to be a specific and independent disclosure of each of the esters of α, β γ or δ glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine in the D and L-configurations.

The term "pharmaceutically acceptable salt or prodrug" is used throughout the specification to describe any pharmaceutically acceptable form (such as an ester, phosphate ester, salt of an ester or a related group) of a compound which, upon administration to a patient, provides the active compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable salts may also be acid addition salts when formed with a nitrogen atom. Such salts are derived from pharmaceutically acceptable inorganic or organic acids, such as hydrochloric, sulfuric, phosphoric, acetic, citric, tartaric, and the like. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

Preparation of the Compounds (i) Synthesis of
3,5-Di-O-protected-D-ribono-γ-lactone Wittig reaction of 2,3-O-isopropylidene-D-glyceraldehyde 39 (Scheme 4) with commercially available 40 affords the (E)-product 41 as a major product. Sharpless dihydroxylation (J. Org. Chem. 1992, 57, 2768-2771) using AD-mix-β as a dihydroxylation reagent gives only the desired product 42 in very high yield. High yield lactonization of 42 to 2-C-methyl-D-arabino-γ-lactone (46) is achieved by HCl/MeOH treatment. Selective O-benzoylation of primary and secondary OH groups yields 3,5-di-O-benzol derivative 47 in high yield. Treatment of 47 with DAST or Deoxofluor, [bis(2-methoxyethyl)amino]sulfur trifluoride, under various conditions gives trace amounts of the desired 2'-fluoro-ribono-γ-lactone 49, but mostly a mixture from which the non-fluorinated ribonolactone (48) is isolated. However, treatment of 47 with excess, preferably three (3) equivalents, of tertiary amine, preferably diisopropylethylamine, and excess, preferably five (5) equivalents, of DAST or Deoxofluor provides 49 in ~50% yield. It was also found that using 3,5-O-MOM instead of benzoyl protection, the yield of 48 approaches 90%. Thus, treatment of 46 with dimethoxymethane in the presence of strong acid such as trifluoromethylsulfonic acid affords 50, which upon reaction with DAST or Deoxofluor in the presence of base yielded 87% isolated yield of 49.

It was also discovered that smooth fluorination can occur upon treatment of the open-chain monobenzoate 43, which can be readily obtained by selective benzoylation of 42, with DAST or Deoxofluor giving rise to the desired ethyl 2-deoxy-2-fluoro-2-C-methyl-3-O-benzoyl-4,5-O-isopropylidene-D-ribonate 44. Lactonization of 44 gives only the γ-lactone 45. Further benzoylation of 45 affords dibenzoate 49.

Fluorination of 55 is performed at the 2-position using an electrophilic fluorination ("F+") in an appropriate solvent such as dimethylformamide, tetrahydrofuran, ethanol, tert-butanol, or diethyl ether or any combination of these solvents known to those skilled in the art (Rozen, et. al., *J. Org. Chem.*, 2001, 66, 7646-7468; Jun-An Ma and Dominique Cahard, *Journal of Fluorine Chemistry*, 2004, in press, and references cited therein), to afford 56. Some non-limiting examples of electrophilic fluorinating reagents are Selectflour®, N-fluorosulfonimide (NFSI), and AcOF. Stereoselective fluorination can be achieved by using a catalyst such as an asymmetric

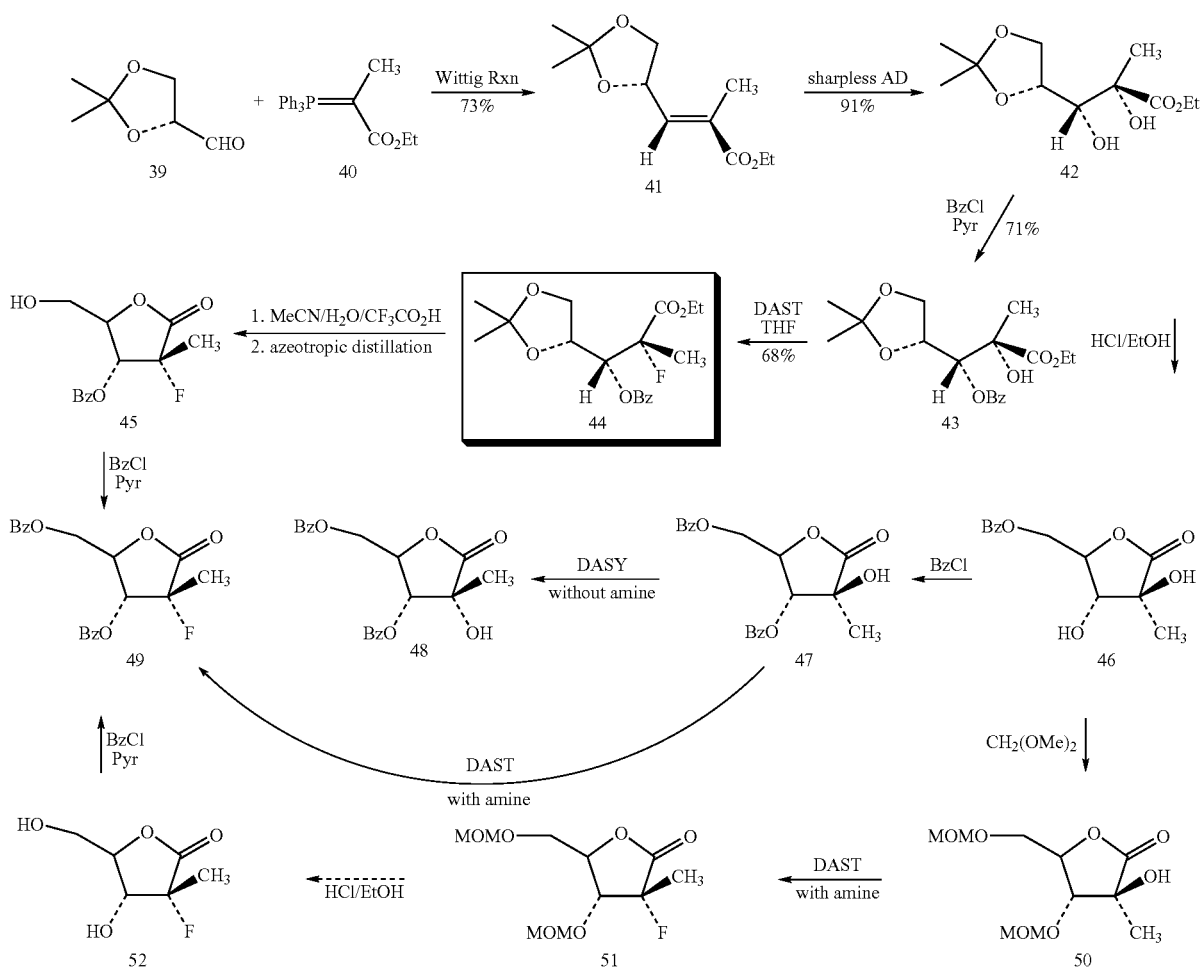

Scheme 4

In one embodiment of the present invention, a method is provided for the synthesis of intermediate 49 through Reformatsky condensation of 39 with an alkyl 2-bromopropionate such as 53 (Scheme 5) in the presence of activated zinc in an ethereal solvent such as diethyl ether or tetrahydrofuran (or a mixture of the two solvents) to give 54, which is converted to 55 by oxidation. Possible oxidizing agents are: activated dimethylsulfoxide, such as a mixture of dimethylsulfoxide, trifluoroacetic anhydride or acetic anhydride (a Swern/Moffat oxidation); chromium trioxide or other chromate reagent; Dess-Martin periodinane; or tetrapropylammonium perruthenate (TPAP) with or without molecular sieves. This oxidation to provide the C-3 ketone preferably proceeds without affecting the stereochemistry at C-4.

transition metal complex catalyst as taught by Sodeoka, et al. (JP2004010555) or by other catalysts. The starting β-keto ester 55 may also be first converted to a ketene silyl acetal prior to fluorination (Rozen, et. al., *J. Org. Chem.*, 2001, 66, 7646-7468).

Selective reduction of the C-3 ketone 56 using triphenylsilane in the presence of a Lewis acid such as AlCl₃ or in the presence of an organic acid such as trifluoroacetic acid (Kitazume, et al., *J. Org. Chem.*, 1987, 52, 3218-3223) provides two 2,3 anti products 57 and 58. However, by utilizing a stereoselective fluorination combined with the selective reduction, a good yield (with high diastereomeric excess) of 58 can be achieved. Benzoylation of 58 gives 44 which is converted to lactone 45 as described earlier.

Scheme 5

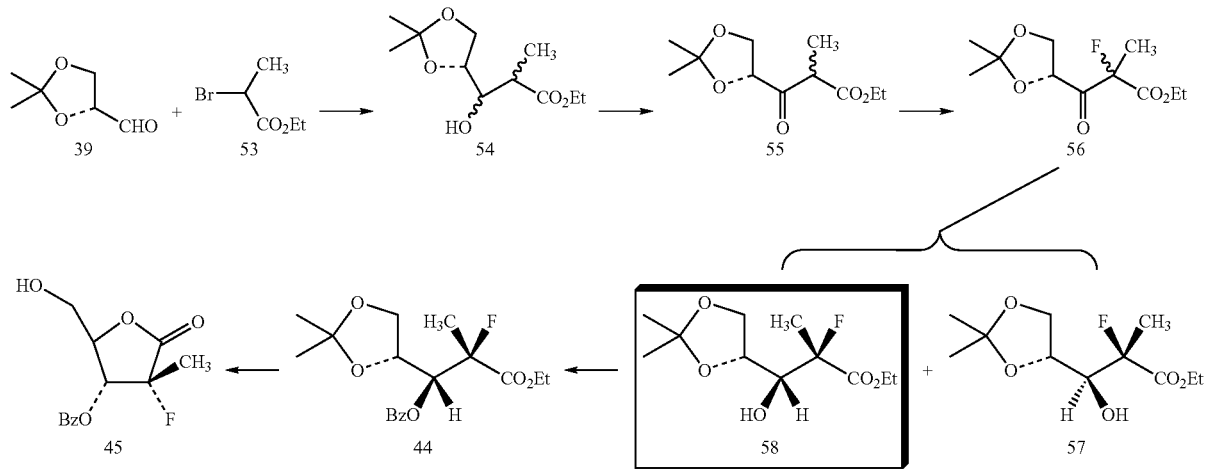

(ii) Preparation of Nucleosides Containing 2-deoxy-2-fluoro-3-methyl-D-ribofuranosyl Moiety by Condensation A lactone such as 49 can be reduced to the corresponding lactol with DIBAL-H. After acetylation of the anomeric hydroxyl group, 59 (Scheme 6) is obtained in high yield.

Condensation of 59 with silylated base (e.g., silylated $N^4$-benzoylcytosine under Vorbrüggen's conditions) affords a mixture of protected anomeric nucleosides 60 and 60-α. After separation of the anomers, the desired β-nucleoside 14 is prepared by deprotection with metal alcoholate in alcohol, preferably NaOMe/MeOH, or methanolic ammonia.

Scheme 6

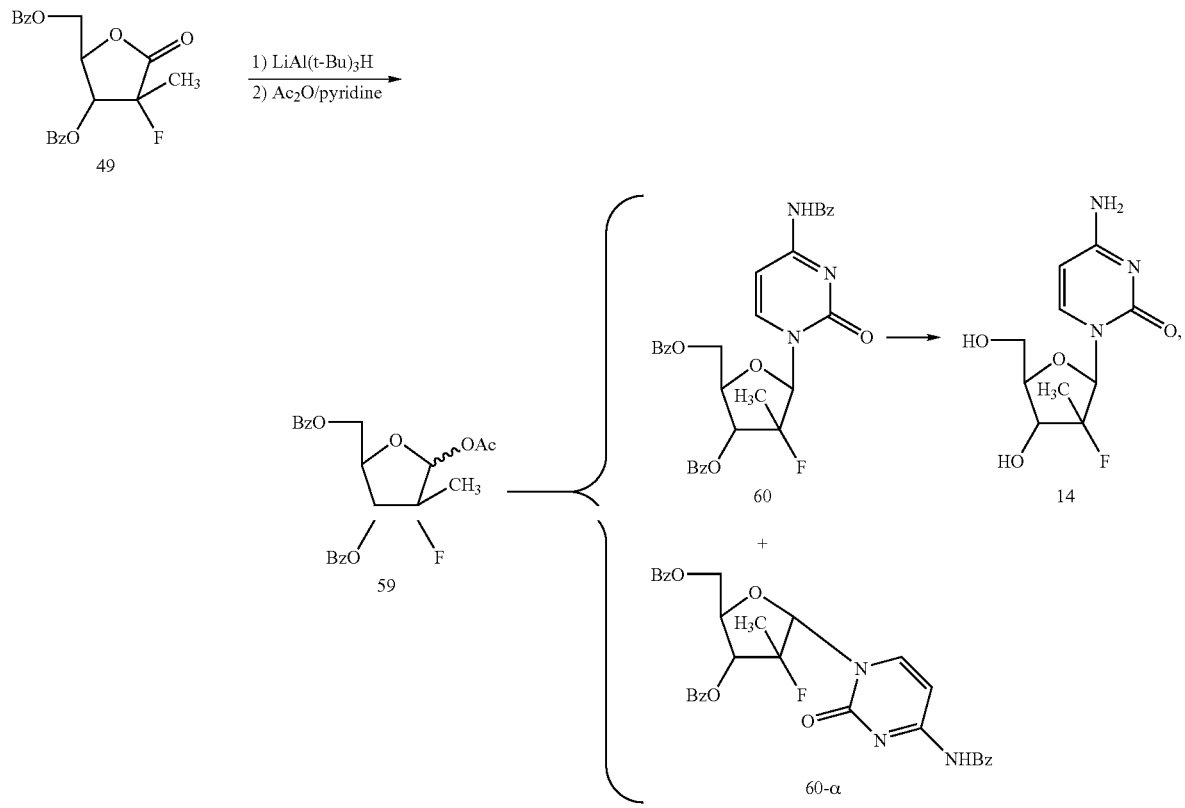

Compound 59 can be converted into the bromo sugar 61, (Scheme 7) which is condensed with a sodium salt of purine, e.g., sodio-N6-benzoyladenine to give the corresponding protected purine nucleoside 62. The desired free nucleoside 63 is readily obtainable by saponification.

(iii) Synthesis from Preformed Nucleosides

Using preformed nucleosides as starting materials for preparation of the desired 2'-C-alkyl-2'-deoxy-2'-fluoro-β-D-ribonucleosides has certain advantages, as the formation of anomers and their subsequent separation can be circumvented, resulting in high yields of the targeted nucleosides.

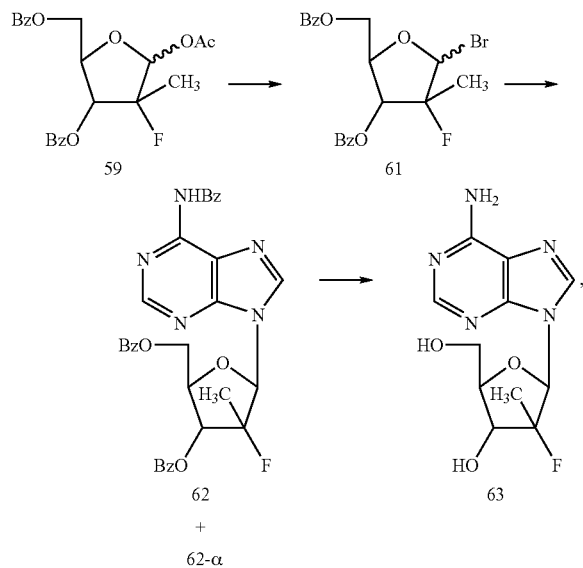

Two procedures to prepare the desired nucleoside 14 from nucleoside starting materials have been disclosed (Schemes 2 and 3). As mentioned earlier, however, these procedures also produced two undesirable products 22 and 23, the latter produced by neighboring group participation as shown in Scheme 8. The separation of the desired nucleoside 14 from the mixture is rather cumbersome. Thus, this invention prevents production of 23 using non-participating protecting group, such as THP, methyl, ethyl, benzyl, p-methoxybenzyl-, benzyloxymethyl, phenoxymethyl, methoxymethyl, ethoxymethyl, mesyl, tosyl, trifluoroacetyl, trichloroacetyl, at the 3'-OH group.

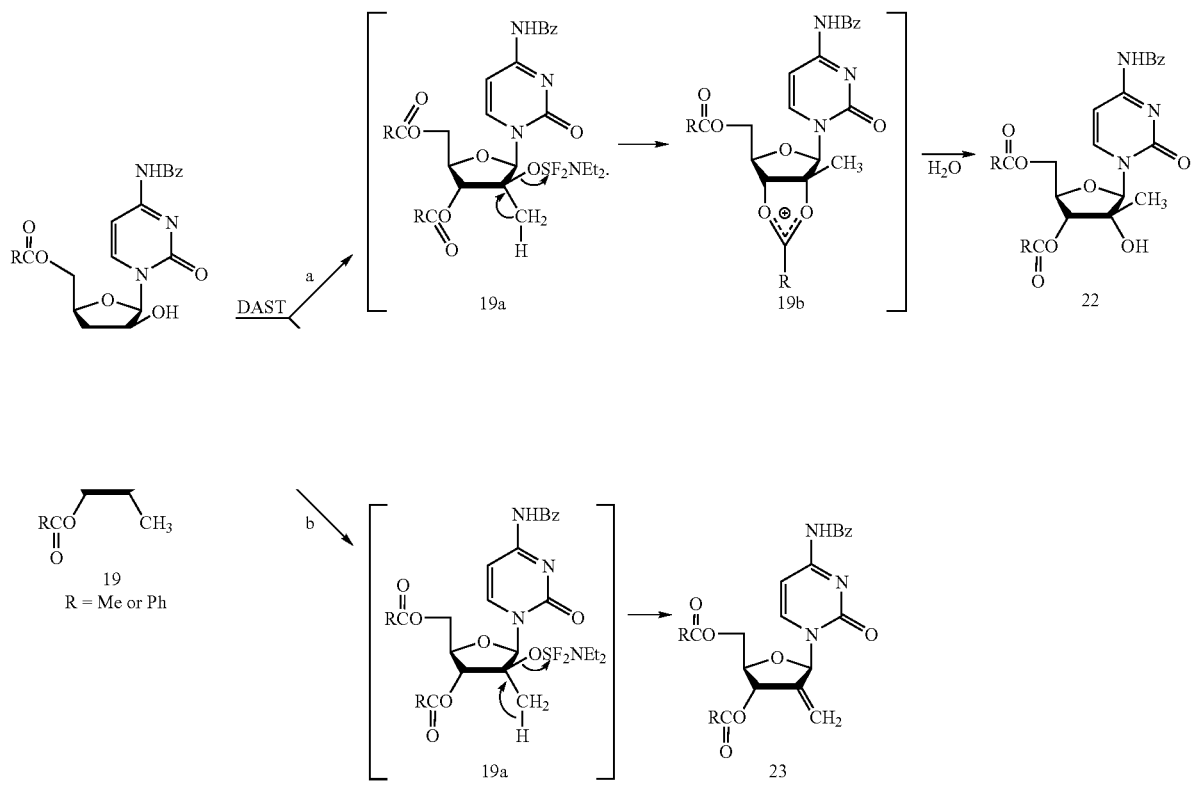

An example is shown in Scheme 9. When N⁴,5'-O-dibenzoyl-3'-O-mesyl-2'-deoxy-2'-C-methyl-β-D-arabinofuranosylcytosine (64) is treated with DAST or Deoxofluor, the desired fluorinated product 65 is obtained in 54% yield along with the olefin 66 in 39% yield. As expected, no unfluorinated cytidine derivative 67 is formed in detectable amounts. There are several ways to de-protect 65 to 14. An example is shown in Scheme 9 that requires a double inversion of the 3'-configuration.

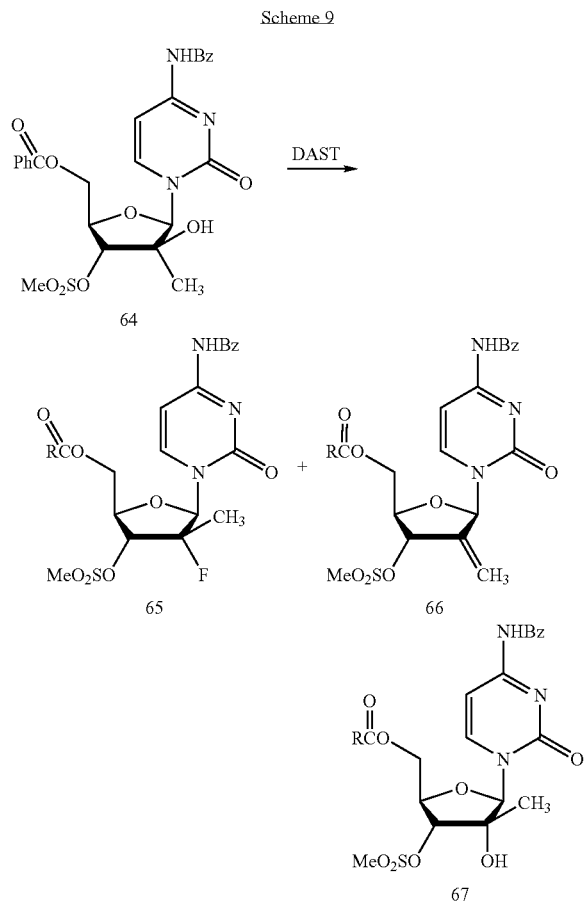

Scheme 9

When the 3'-O-substituent is a non-participating and non-leaving group, such as methoxymethyl (MOM), methyl, benzyl, methoxybenzyl or tetrahydropyranyl, the intermediate is fluorinated more effectively than 64.

The following examples are presented to illustrate the present invention but are not to be limited thereto.

Experimental: 2,3-O-Isopropylidene-D-glyceraldehyde (39) is prepared by literature procedures (Organic Synthesis, Annual Volume 72, page 6; J. Org. Chem. 1991, 56, 4056-4058) starting from commercially available protected D-mannitol. Other reagents, including 40 and AD-mix-β, are from commercial sources.

EXAMPLES

Example 1

Ethyl trans-2,3-dideoxy-4,5-O-isopropylidene-2-C-methyl-D-glycero-pent-2-enonate (41)

To a solution of (carbethoxyethylidene)triphenylphosphorane (40, 25 g, 69 mmol) in dry $CH_2Cl_2$ (65 mL) at room temperature is added dropwise a solution of 2,3-O-isopropylidene-D-glyceraldehyde (39, 9.41 g, 72.3 mmol) in $CH_2Cl_2$ (30 mL). The mixture is stirred at room temperature overnight. The reaction mixture is then concentrated to dryness, diluted with light petroleum ether (300 mL), and kept at room temperature for 2 h. Triphenylphosphine oxide precipitated is removed by filtration and an aliquot is concentrated in vacuo. The residue is purified by silica gel column chromatography with 0-1.5% EtOAc in hexanes to give 41 (10.4 g, 71%) as an oil (Carbohydrate Res., 115, 250-253 (1983)). ¹H NMR ($CDCl_3$) δ 1.30 (t, J=6.8 Hz, 3H, —$OCH_2CH_3$, 1.41 (, s, 3H, $CH_3$), 1.45 (,s, 3H, $CH_3$), 1.89 (d, J=1.2 Hz, 3H, 2-$CH_3$), 3.63 (t, J=8.0 Hz, 1H, H-5), 4.14-4.23 (m, 3H, H-5' and —O$CH_2CH_3$), 4.86 (dd, J=7.6 and 13.6 Hz, 1H, H-4), 6.69 (dd, J=1.6 and 8.0 Hz, 1H, H-3), Example 2

(2S,3R)-3-[(4R)-2,2-Dimethyl-[1,3]dioxolan-4-yl]-2,3-dihydroxy-2-methyl-propionic acid ethyl ester (42)

A round-bottomed flask, equipped with a magnetic stirrer, is charged with 25 mL of t-BuOH, 25 mL of water, and 7.0 g of AD-mix-β. Stirring at room temperature produced two clear phases; the lower aqueous phase appears bright yellow. Methanesulfonamide (475 mg) is added at this point. The mixture is cooled to 0° C. whereupon some of the dissolved salts precipitated, 1.07 g (5 mmol) of 41 is added at once, and the heterogeneous slurry is stirred vigorously at 0° C. for 24 h. After this time, while the mixture is stirred at 0° C., solid sodium sulfite (7.5 g) is added and the mixture allowed to warm to room temperature and stirred for 30-60 min. EtOAc (50 mL) is added to the reaction mixture, and after separation of the layers, the aqueous phase is further extracted with EtOAc. The organic layer is dried over $Na_2SO_4$ and concentrated to dryness. The residue is purified by silica gel column chromatography with 20% EtOAc in hexanes to provide 42 (1.13 g, 91%) as a solid. ¹H NMR (DMSO-$d_6$) □ 1.18 (t, J=6.8 Hz, 3H, —$OCH_2CH_3$, 1.24 (, s, 3H, $CH_3$), 1.25 (, s, 3H, $CH_3$), 1.28 (s, 3H, 2-$CH_3$), 3.67 (t, J=7.2 Hz, 1H), 3.85, 4.06 and 4.12 (m, 4H), 4.96 (s, 1H, 2—OH, $D_2O$ exchangeable), 5.14 (d, J=7.6 Hz, 2-OH, $D_2O$ exchangeable). Anal. Calcd for $C_{11}H_{20}O_6$: C, 53.22; H, 8.12. Found: C, 53.32; H, 8.18.

Example 3

(2S,3R)-3-[(4R)-2,2-Dimethyl-[1,3]dioxolan-4-yl]-3-benzoyloxy-2-hydroxy-2-methylpropionic acid ethyl ester (43)

To a solution of compound 42 (245 mg, 0.99 mmol) in dry pyridine (3 mL) is added dropwise a solution of BzCl (300 mg, 2.1 mmol) in pyridine (1 mL). After the mixture is stirred at room temperature for 2 h, the reaction is quenched with $H_2O$ (1 mL). The mixture is concentrated to dryness and the residue is partitioned between $CH_2Cl_2$ and sat. $NaHCO_3$ solution. The organic phase is dried (anh. $Na_2SO_4$), filtered and concentrated. The residue is purified by silica gel column chromatography with 5% EtOAc in hexanes to give 43 (247 mg, 71%) as a solid. Anal. Calcd for $C_{18}H_{24}O_7$: C, 61.35; H, 6.86. Found: C, 60.95; H, 6.73.

Example 4

(2R,3R)-3-[(4R)-2,2-Dimethyl-[1,3]dioxolan-4-yl]-3-benzoyloxy-2-fluoro-2-methyl-propionic acid ethyl ester (44)

To a solution of compound 43 (36 mg, 0.102 mmol) in anhydrous THF (1.5 mL) is added DAST or Deoxofluor (0.08 mL, 0.68 mmol) at 0° C. under argon. The reaction mixture is stirred at room temperature for 3 h, then cooled down to 0° C., and carefully treated with cold saturated NaHCO$_3$ solution (2 mL). The organic layer is dried over Na$_2$SO$_4$ and concentrated to dryness. The residue is purified by silica gel column chromatography with 1-3% EtOAc in hexanes to give 44 (24.6 mg, 68%) as a syrup. HR-FAB MS; Obsd: m/z 361.1621. Calcd for C$_{18}$H$_{23}$O$_6$FLi: m/z 361.1639 (M+H)$^+$.

Example 5

3-O-Benzoyl-2-methyl-2-deoxy-2-fluoro-D-ribono-γ-lactone (45)

A mixture of compound 44 (308 mg, 0.86 mmol), MeCN (20 mL), water (1 mL) and CF$_3$CO$_2$H (0.17 mL) is refluxed at 80-85° C. for 3 h. The open-chain intermediate is not isolated, but converted directly to 45 by azeotropic distillation using a Dean-Stark water separator. The removed MeCN is replaced with dry toluene, and the azeotropic distillation continued until the oil bath temperature reached 130° C. Stirring at 130° C. is continued overnight. The mixture is then cooled to room temperature and the solvent is removed in vacuo to give a syrup, which is purified by silica gel column chromatography with 10-15% EtOAc in hexanes to give, after solvents evaporation, solid 45 (136 mg, 58.3%).

Example 6

3,5-Di-O-benzoyl-2-methyl-2-deoxy-2-fluoro-D-ribono-γ-lactone (49)

To a solution of 45 (60 mg, 0.224 mmol) in EtOAc (1 mL) are added pyridine (100 mg, 1.26 mmol) and 4-dimethylaminopyridine (2.7 mg). The mixture is warmed to 60° C. and BzCl (110 mg, 0.79 mmol) in EtOAc (0.4 mL) is added dropwise. After stirring for 3 h, the mixture is cooled to 0° C. and pyridine HCl salt is filtered off. The filtrate is diluted with EtOH and the mixture is evaporated to dryness. The residue is purified by silica gel column chromatography with 3-6% EtOAc in hexanes to provide, after solvents evaporation, solid 49 (75 mg, 91%).

Example 7

2-Methyl-D-arabino-γ-lactone (46)

A solution of compound 42 (248 mg, 1 mmol) in 1.5 mL of EtOH is treated with 0.3 mL of concentrated HCl. The reaction mixture is stirred at room temperature for 2 h. The solvent is removed in vacuo (bath temp. <45° C.). The residue is co-evaporated with toluene (3×10 mL) to give a residue, which is purified by silica gel column chromatography with 70% EtOAc in hexanes. Evaporation of solvents give oily 46 (170 mg, 105%). Anal. Calcd for C$_6$H$_{10}$O$_5$: C, 41.24; H, 6.22. Found: C, 41.00; H, 6.74.

Example 8

3,5-Di-O-benzoyl-2-methyl-D-arabino-γ-lactone (47)

To a stirred solution of compound 46 (880 mg, 5.4 mmol) in dry pyridine (80 mL) is added dropwise a solution of BzCl (1.73 g, 12.29 mmol) in dry pyridine (45 mL) at room temperature over a period 75 min. The mixture is stirred for another 90 min, then treated with MeOH (5 mL), and concentrated to dryness. The residue is purified by silica gel column chromatography with 12-20% EtOAc in hexanes to give 47 (1.1 g, 55%) as an oil.

Example 9

3,5-Di-O-benzoyl-2-deoxy-2-fluoro-2-C-methyl-D-ribonolactone (49)

To a solution of 47 (430 mg, 1.16 mmol) in anhydrous THF (20 mL) and diisopropylethylamine (1 mL, 5.74 mmol) is added DAST or DEOXOFLUOR (0.48 mL, 3.66 mmol) at room temperature under argon. The reaction mixture is stirred at room temperature for 3 h, then cooled down to 0° C., and carefully treated with cold saturated NaHCO$_3$ solution (5 mL). The reaction mixture is partitioned between EtOAc (100 mL) and water (20 mL). The organic layer is dried over (Na$_2$SO$_4$) and concentrated to dryness. The residue is purified by silica gel column chromatography with 3-6% EtOAc in hexanes to provide 49 (220 mg, 51%) as a solid.

Example 10

3,5-Di-O-benzoyl-2-methyl-D-ribono-lactone (48)

To a solution of 47 (160 mg, 0.432 mmol) in anhydrous CH$_2$Cl$_2$ (5 mL) is added DAST or DEOXOFLUOR (0.15 mL, 1.14 mmol) at 0-5° C. under argon. The reaction mixture is stirred at 0-5° C. for 1 h then at room temperature. After 24 hrs, the reaction still does not go well as there is no major less polar product appears in the TLCs. The reaction mixture is cooled to 0° C., and carefully treated with cold saturated NaHCO$_3$ solution. The organic layer is dried over Na$_2$SO$_4$ and concentrated to dryness. The residue is checked by proton NMR. It shows that the major product is 3,5-dibenzoyl-2-methyl-D-ribono-γ-lactone (48), which is identical with authentic sample. Traces of 49 are detected on the spectrum.

Example 11

3,5-Di-O-methoxymethyl-2-C-methyl-D-arabino-γ-lactone (50)

To a solution of 2-methylarabinolactone (46) (324 mg, 2 mmol) in CH$_2$(OMe)$_2$ (30 mL) and CH$_2$Cl$_2$ (30 mL) was added CF$_3$SO$_3$H (50 μL), and the solution was stirred at RT under argon for 14 h. The reaction was quenched by addition of 28% NH$_4$OH (0.1 mL), and the mixture was dried by addition of Na$_2$SO$_4$. After removal of the solvent by evaporation, the residue was purified by flash chromatography on silica gel eluting with CH$_2$Cl$_2$/MeOH (95:5 to 9:1) to give 450 mg (90%) of product as a pale yellow oil. $^1$H-NMR (DMSO-d$_6$): 6.10 (s, OH, D$_2$O exchangeable), 4.70 (q, 2H, CH$_2$), 4.62 (d, 2H, CH$_2$), 4.30 (m, 1H, H-4), 4.20 (d, 1H, H-3), 3.80-3.65 (m, 2H, H-5), 3.30, 3.28 (2s, 6H, 2 CH$_3$), 1.26 (s, 3H, CH$_3$).

Example 12

3,5-Di-O-methoxymethyl-2-deoxy-2-fluoro-2-C-methyl-D-ribono-γ-lactone (51)

To a solution of 50 (100 mg, 0.4 mmol) in CH$_2$Cl$_2$ (3 mL) and pyridine (0.5 mL) at −78° C. is added DAST or DEOXOFLUOR (0.21 mL, 1.6 mmol), and the solution is stirred at −78° C. for 15 min. Then the solution is allowed to warm up to room temperature and stirred at room temperature for 2 h. The reaction is quenched by addition of saturated aqueous NaHCO$_3$ (0.5 mL) and ice-water (0.5 mL), followed by CH$_2$Cl$_2$ (20 mL) and saturated aqueous NaHCO$_3$ (10 mL). The aqueous layer is extracted with CH$_2$Cl$_2$ twice, the combined organic layers are washed with NaHCO$_3$, and dried over Na$_2$SO$_4$. The evaporation of the solvent gives 51 (88 mg, 87%) as a brownish-yellow oil. $^1$H-NMR (DMSO-d$_6$): 4.74 (q, J=6.9 & 18.1 Hz, 2H, CH$_2$), 4.63 (d, J=0.77 Hz, 2H, CH$_2$), 4.54 (m, 1H, H-4), 4.18 (dd, J=7.8 & 20.0 Hz, 1H, H-3), 3.86-3.71 (m, 2H, H-5), 3.34, 3.28 (2s, 6H, 2 CH$_3$), 1.59 (d, J=24.26 Hz, 3H, CH$_3$).

Example 13

Ethyl 4,5-O-Isopropylidene-3,4,5-trihydroxy-2-methylvalerate (54)

To activated zinc (6.5 g, 0.10 mmol) is added about 20 mL of a solution containing 39 (13.0 g, 0.1 mmol), 53 (13.0 mL, 0.10 mmol), THF (50 mL), and diethyl ether (50 mL). After the addition, one crystal of 12 is added, whereby an exotherm is generated, causing the solution to reflux. The remaining solution is added over about 0.75 h as to maintain a gentle reflux. The mixture is gently heated to reflux for an additional 1 h after the final addition. The mixture is cooled to room temp, poured into ice (200 mL) and 1 N HCl (200 mL) and allowed to stir until most of the ice had melted (about 0.5 h). The organic layer is separated and the aqueous layer is extracted with diethyl ether (2×75 mL). The combined organic layers are washed with satd NaHCO$_3$ (1×150 mL), brine (1×150 mL), dried (Na$_2$SO$_4$), filtered, and concentrated to dryness in vacuo. Further drying in vacuo provides 54 as a mixture of diastereomers (15.1 g, 65.1%). This compound is used without further purification.

Example 14

Ethyl 4,5-O-Isopropylidene-3-oxo-2-methylvalerate (55)

Compound 54 (9.85 g, 0.042 mol) is dissolved in dry THF (50 mL). Anhydrous DMSO (16.0 mL, 0.22 mol) is added and the resulting solution is cooled to between −20° C. and −15° C. Trifluoroacetic anhydride (9.8 mL, 0.69 mol) is added dropwise over 15 minutes and the solution is stirred between −20° C. and −15° C. for 2 h after which anhydrous NEt$_3$ (24.0 mL, 0.17 mol) is added over 20 min. The resulting solution is stirred at room temp for 1 h, diluted with diethyl ether (50 mL), and washed with H$_2$O (3×100 mL), dried (Na$_2$SO$_4$) and concentrate in vacuo to compound 55 as a yellow oil (8.1 g, 82.0%) that is used without further purification. $^1$H NMR (CDCl$_3$, 400 MHz): δ 1.24-1.38 (m, 26H), 3.81 (q, 1.3; H, J=7.3 Hz), 3.89 (q, 1.0H, J=7.3 Hz), 3.99-4.04 (m, 3H), 4.10-4.20 (m, 7H), 4.21-4.29 (m, 3H), 4.51 (dd, 1.0H, J=8.1, 6.2 Hz), 4.58 (dd, 1.3H, J=7.7, 5.0 Hz).

Example 15

Ethyl 4,5-O-Isopropylidene-2-fluoro-3-keto-2-methylvalerate (56)

Compound 55 (7.36 g, 0.042 mol) is dissolved in anhydrous DMF (5.0 mL) and treated with a slurry of Selectfluor (55.0 g, 0.155 mol) in DMF (45.0 mL). The mixture is placed in an oil bath maintained at 45-50° C. and the suspension is maintained with stirring at that temperature overnight under an argon atmosphere. The solution is concentrated to near dryness in vacuo, treated with diethyl ether (~25 mL) and washed with water (3×100 mL). The organic phase is dried (Na$_2$SO$_4$) and concentrate in vacuo to compound 56 as a yellow oil (5.65 g, 71.2%) that was an approximate 1:1 mixture of 2R:2S fluorinated compound as judged by $^{19}$F NMR. $^1$H NMR (CDCl$_3$, 400 MHz): δ 1.20-1.46 (m, 16H), 1.70 (2d, 3H, J=22.8 Hz), 4.05-4.10 (m, 2H,), 4.12-4.32 (m, 2H,), 4.90-97 (m, 1H). $^{19}$F NMR (CDCl$_3$, 376 MHz, C$_6$F$_6$ external standard): δ 4.30 (q), 4.01 (q).

Example 16

3,5-O-dipivaloyl-2-methyl-D-arabino-γ-lactone (47 B)

To a solution of 42 (4 mmol, 897 mg) in EtOH (20 mL) was added concentrated HCl (2.0 mL), and the solution stirred at room temperature for 1 h. The solution was concentrated to dryness and the residue was co-evaporated with THF (10 mL) and dissolved in pyridine (6 mL) and CH$_2$Cl$_2$ (14 mL). The solution was cooled in ice-bath. To the solution was added pivaloyl chloride (8 mmol, 0.98 mL) and the solution stirred at 0° C. for 30 min. To the solution was added an additional pivaloyl chloride (4 mmol, 0.49 mL) and the solution stirred at room temperature for 5 h. To the solution was added 4-dimethylaminopyridine (100 mg) and the solution was stirred at room temperature for 20 h. H$_2$O (5 mL) was added and the mixture was stirred at room temperature for 20 min. EtOAc (50 mL) was added. The mixture was washed with water, brine and dried (Na$_2$SO$_4$). Solvent was removed and the residue was recrystallized from EtOAc-Hexanes to give fine crystals (625 mg, 47%). H-NMR (CDCl$_3$): δ 5.18 (d, J=6.80 Hz, 1H, H-3), 4.45, 4.22 (m, 2H, H-5), 4.41 (m, 1H, H-4), 3.32 (br s, 1H, OH, D2O exchangeable), 1.43 (s, 1H, Me), 1.25, 1.22 [ss, 18H, C(Me)$_3$].

Example 17

2-Deoxy-3,5-O-dipivaloyl-2-fluoro-2-C-methyl-D-ribono-γ-lactone (49B)

To a solution of 47B (100 mg, 0.3 mmol) in THF (5 mL) were added EtNPr$_2$ (2 mmol, 0.35 mL) and Deoxo-Fluor (0.18 mL, 0.9 mmol), and the solution was stirred at room temperature for 4 h. To the solution was added additional Deoxo-Fluor (0.18 mL, 0.9 mmol) and the solution was stirred at room temperature for 16 h, refluxed for 1 h. EtOAc (50 mL) was added. The solution was washed with aqueous NaHCO$_3$, brine, dried (Na$_2$SO$_4$). Solvent was removed and the residue was purified by column (10% EtOAc in hexanes) to give product as a solid (65 mg, 65%). H-NMR (CDCl$_3$): δ 5.12 (m, 1H, H-3), 4.68 (m, 1H, H-4), 4.41, 4.18 (mm, 2H, H-5), 1.63 (d, J=23.2Hz, 1H, Me), 1.25, 1.20 [ss, 18H, C(Me)$_3$].

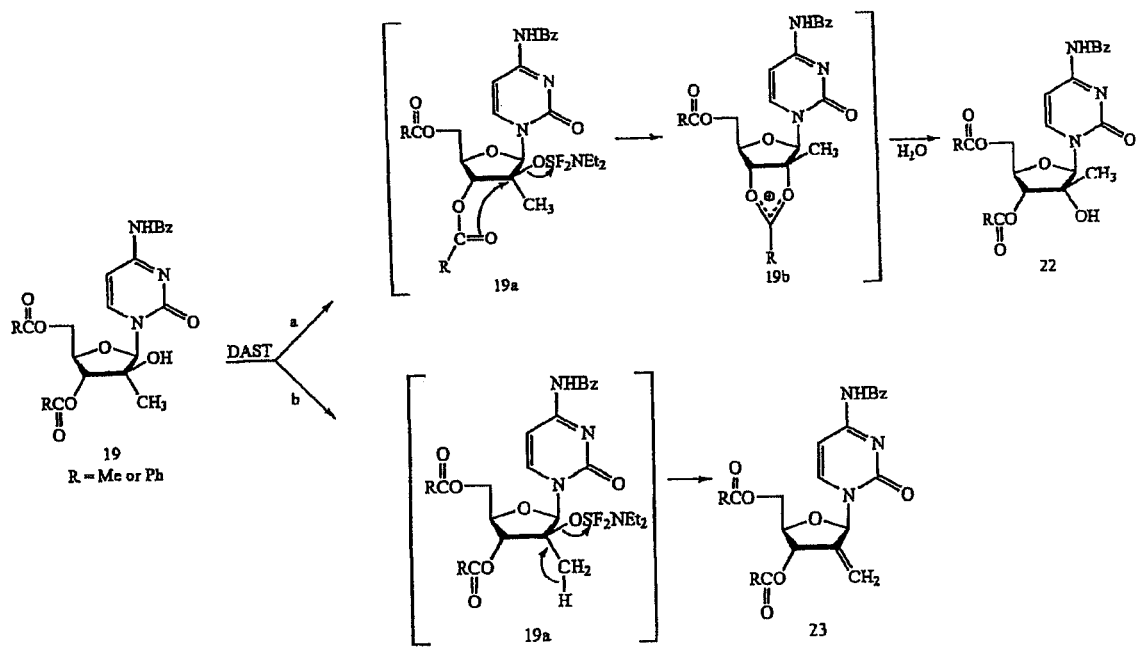

We claim:

1. A compound of the following formula:

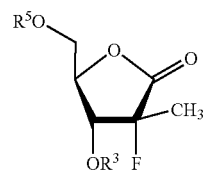

wherein R$^3$ and R$^5$ can be independently H, CH$_3$, benzyl, 4-methoxybenzyl, trityl, trialkylsilyl, t-butyldialkylsilyl, t-butyldiphenylsilyl, tetraisopropyldisilyl (TIPDS), tetrahydropyranyl (THP), methoxymethyl (MOM), β-methoxyethoxymethyl (MEM), or acyl;

alternatively, $R^3$ and $R^5$ are linked through —$SiR_2$—O—$SiR_2$— or —$SiR_2$—, wherein R is a lower alkyl.

2. A compound of claim 1, wherein $R^3$ and $R^5$ are each independently H, $CH_3$, acetyl, benzoyl, pivaloyl, 4-nitrobenzoyl, 3-nitrobenzoyl, 2-nitrobenzoyl, 4-chlorobenzoyl, 3-chlorobenzoyl, 2-chlorobenzoyl, 4-methylbenzoyl, 3-methylbenzoyl, 2-methylbenzoyl, 4-phenylbenzoyl, benzyl, 4-methoxybenzyl, trityl, trialkylsilyl, t-butyl-dialkylsilyl, t-butyldiphenylsilyl, TIPDS, THP, MOM, or MEM.

3. A compound of claim 1, wherein $R^3$ and $R^5$ are each independently H, $CH_3$, acetyl, benzoyl, benzyl, trityl, trialkylsilyl, t-butyl-dialkylsilyl, t-butyldiphenylsilyl, TIPDS, THP, MOM, or MEM.

4. A compound of claim 1, wherein $R^3$ and $R^5$ are each independently H, $CH_3$, acetyl, benzyl, trityl, trialkylsilyl, t-butyl-dialkylsilyl, t-butyldiphenylsilyl, TIPDS, or THP.

5. A compound of claim 1, wherein $R^3$ and $R^5$ are each independently H, $CH_3$, acetyl, benzyl, trityl, trialkylsilyl, t-butyl-dialkylsilyl, t-butyldiphenylsilyl, or TIPDS.

6. A compound of claim 1, wherein $R^3$ and $R^5$ are each independently H, $CH_3$, acetyl, benzyl, trialkylsilyl, t-butyl-dialkylsilyl, t-butyldiphenylsilyl, or TIPDS.

7. A compound of claim 1, wherein $R^3$ and $R^5$ are each independently H, $CH_3$, acetyl, or benzyl.

8. A compound of claim 1, wherein $R^3$ and $R^5$ are each independently H, $CH_3$, or acetyl.

9. A compound of claim 1, wherein $R^3$ and $R^5$ are each independently H or $CH_3$.

10. A compound of claim 1, wherein $R^3$ and $R^5$ are H.

11. A compound of claim 1, wherein $R^3$ and $R^5$ are $CH_3$.

12. A compound of claim 1, wherein $R^3$ and $R^5$ are acetyl.

13. A compound of claim 1, wherein $R^3$ and $R^5$ are benzyl.

14. A compound of claim 1, wherein $R^3$ and $R^5$ are acyl.

15. A compound of claim 1, wherein $R^3$ and $R^5$ are linked through —$SiR_2$—O—$SiR_2$— or —$SiR_2$—, and wherein R is selected from among methyl, ethyl, n-propyl, and i-propyl.

16. A process for the preparation of the compound of claim 1 wherein $R^5$ is H and $R^3$ is Bz, comprising the steps of:

(a) reacting a compound of the formula, 39,

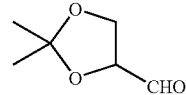

with an alkyl-2-bromopropionate in the presence of activated zinc in a solvent;

(b) adding an oxidizing agent to provide a ketone;

(c) fluorinating the product of step (b) to produce a fluorinated ketone;

(d) reducing the fluorinated ketone of step (c); and (e) benzylating the product of step (d).

17. The process of claim 16, wherein the solvent of step (a) is selected from the group consisting of diethyl ether and tetrahydrofuran.

18. The process of claim 16, wherein the oxidizing agent of step (b) is selected from the group consisting of: an activated dimethylsulfoxide, a chromatic agent, a Dess-Martin periodione, and tetrapropylammonium perruthenate.

* * * * *

UNITED STATES PATENT AND TRADEMARK OFFICE
CERTIFICATE OF CORRECTION

PATENT NO. : 7,601,820 B2
APPLICATION NO. : 11/353597
DATED : October 13, 2009
INVENTOR(S) : Peiyuan Wang et al.

It is certified that error appears in the above-identified patent and that said Letters Patent is hereby corrected as shown below:

The typographical errors are as follows:

1) Column 9, ln. 39, "Z is, halogen, OH, OR', SH, SR', NH$_2$, NHR', or R'" should read "Z is halogen, OH, OR', SH, SR', NH$_2$, NHR', or R'";

2) Column 13, ll. 38–39, "N$^6$-allcylaminopurine, N$^6$-thioallcyl purine" should read "N$^6$-allylaminopurine, N$^6$-thioallyl purine";

3) Column 13, ln. 42, "4-mercaptopyrmidine" should read "4-mercaptopyrimidine";

4) Column 13, ln. 48, "C$^6$-Br-vinyl pyriniidine" should read "C$^6$-Br-vinyl pyrimidine";

5) Column 14, ln. 56, "3,5-di-O-benzol derivative 47" should read "3,5-di-O-benzoyl derivative 47";

6) Columns 15 and 16, Scheme 4, third row,

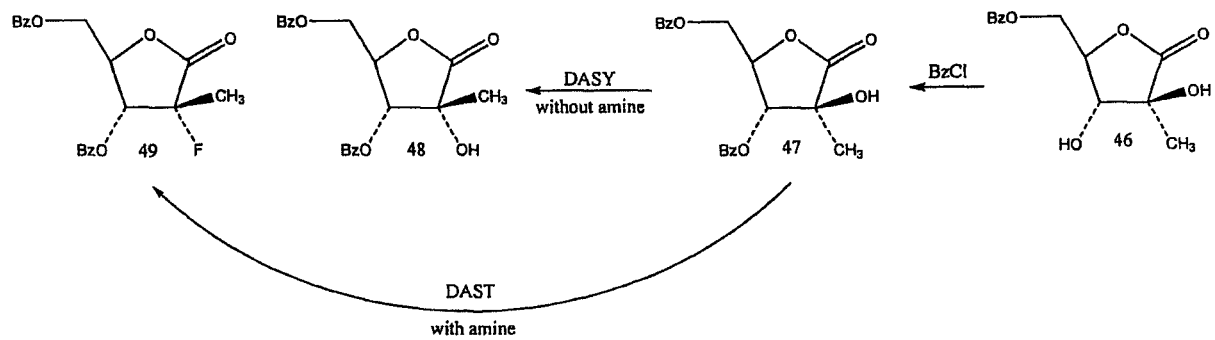

should read

Signed and Sealed this
First Day of March, 2011

David J. Kappos
*Director of the United States Patent and Trademark Office*

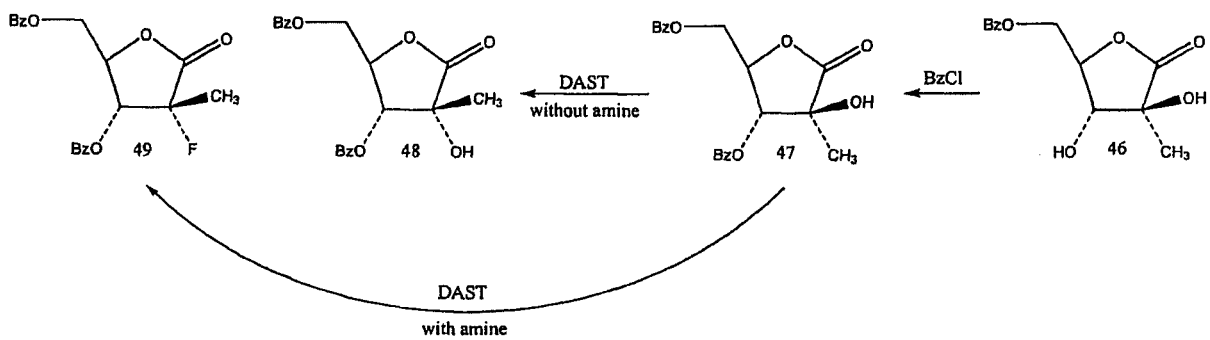

7) Column 21, ll. 63–64 "Ethyl trans-2,3-dideoxy-4,5-O-isopropylidene-2-C-methyl-D-glycero-pent-2-enonate (41)" should read "Ethyl trans-2,3-dideoxy-4,5-O-isopropylidene-2-C-methyl-D-glycero-pent-2-enoate (41)";

8) Column 22, ln. 37 "¹HNMR(DMSO-d₆) □ 1.18" should read "¹H NMR (DMSO-d₆) δ 1.18";

9) Claim 18, Column 28, ll. 31–32 "a Dess-Martin periodione" should read "a Dess-Martin periodinane";

The printing errors made by the PTO are as follows:

10) Column 17, Scheme 6, compound 59,

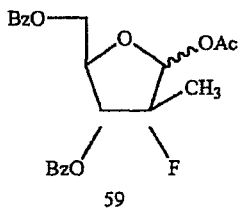

should read

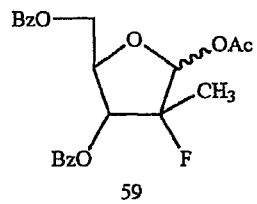

CERTIFICATE OF CORRECTION (continued)
U.S. Pat. No. 7,601,820 B2

11) Columns 19 and 20, Scheme 8,

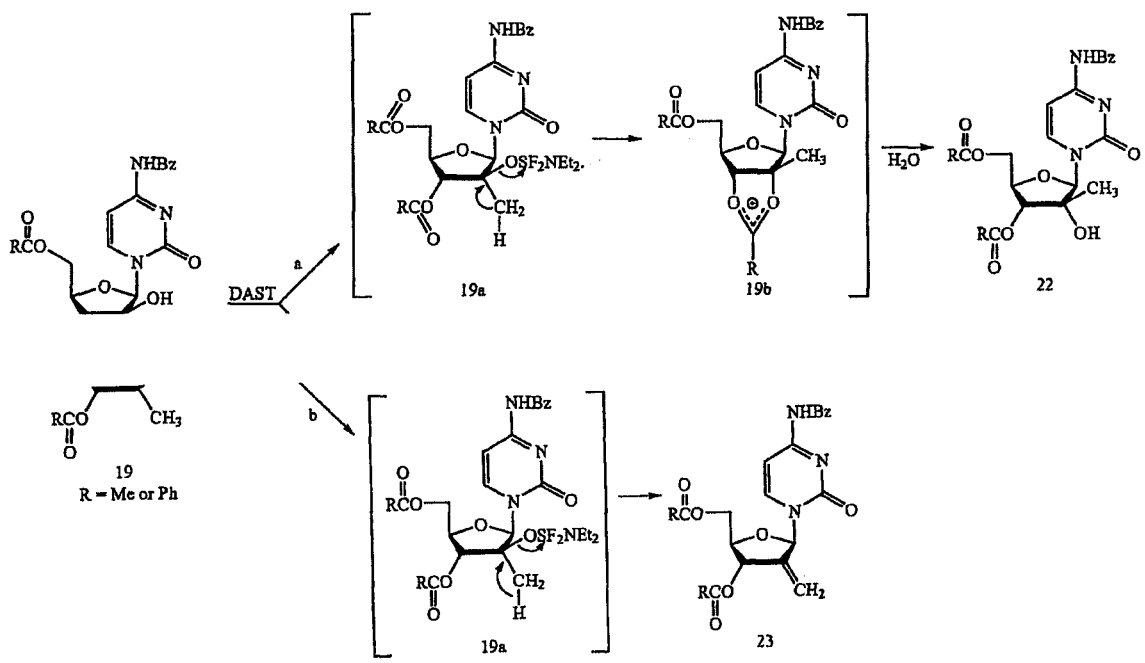

should read